United States Patent [19]

Montanari et al.

[11] Patent Number: 5,674,909
[45] Date of Patent: Oct. 7, 1997

[54] DERIVATIVES OF 2-AMINO-1,2,3,4-TETRAHYDRONAPHTHALENE ACTIVE ON THE CARDIOVASCULAR SYSTEM

[75] Inventors: Stefania Montanari; Paolo Cavalleri, both of Milan; Cristina Fraire, Legnano; Gian Carlo Grancini, Nova Milanese; Mauro Napoletano; Francesco Santangelo, both of Milan, all of Italy

[73] Assignee: Zambon Group, Bresso, Italy

[21] Appl. No.: 465,636

[22] Filed: Jun. 6, 1995

[30] Foreign Application Priority Data

Sep. 13, 1994 [IT] Italy ............... MI94A1868

[51] Int. Cl.$^6$ .............. A61K 31/335; A61K 31/495; A61K 31/10; A61K 31/135
[52] U.S. Cl. .............. 514/649; 514/650; 514/651; 564/337; 564/340; 564/341; 564/342; 564/344; 564/345; 564/346; 564/347; 564/354; 564/367
[58] Field of Search .................. 564/337, 340, 564/341, 342, 344, 345, 346, 347, 354, 367; 514/649, 650, 651

[56] References Cited

U.S. PATENT DOCUMENTS

| | | | |
|---|---|---|---|
| 4,803,225 | 2/1989 | Dixon et al. | 514/654 |
| 5,013,760 | 5/1991 | Farmer et al. | 514/649 |
| 5,070,106 | 12/1991 | Casagrande et al. | 514/651 |
| 5,151,414 | 9/1992 | Casagrande et al. | 514/114 |
| 5,358,971 | 10/1994 | Peck et al. | 514/651 |
| 5,407,956 | 4/1995 | Santangelo et al. | 514/510 |
| 5,451,608 | 9/1995 | Santangelo et al. | 514/674 |

FOREIGN PATENT DOCUMENTS

| | | |
|---|---|---|
| 0072061 | 2/1983 | European Pat. Off. . |
| 0142283 | 3/1985 | European Pat. Off. . |
| 0321968 | 6/1989 | European Pat. Off. . |
| 1509454 | 5/1978 | United Kingdom . |
| 9319036 | 9/1993 | WIPO . |
| 9507885 | 3/1995 | WIPO . |

OTHER PUBLICATIONS

The Merck Index, Eleventh Ed., No. 3418, p. 538 (1989).
Drugs 39(2): 308–330 (1990), Andrew Fitton & Paul Benfield.
Drugs of the Future, vol. 12, No. 3 (1987), H. E. Katerinopoulos & D. Schuster, pp. 223–253.

Primary Examiner—Richard Raymond
Attorney, Agent, or Firm—Watson Cole Stevens Davis, P.L.L.C.

[57] ABSTRACT

Compounds of formula

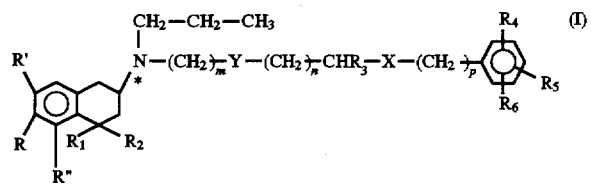

wherein R, R', R", $R_1$, $R_2$, $R_3$, $R_4$, $R_5$, $R_6$, X, Y, m, n and p have the meanings reported in the description;
and their pharmaceutically acceptable salts are described.

The compounds of formula I are useful in the treatment of arterial hypertension and congestive heart failure, of renal failure, of peripheral arteriopathies, of cerebrovascular insufficiencies and of ischemic cardiopathy.

8 Claims, No Drawings

DERIVATIVES OF 2-AMINO-1,2,3,4-TETRAHYDRONAPHTHALENE ACTIVE ON THE CARDIOVASCULAR SYSTEM

The present invention relates to compounds active on the cardiovascular system and, in particular, it relates to derivatives of 2-amino-1,2,3,4-tetrahydro-naphthalene and to their use in therapeutic field.

It is known that some hydroxylated 2-amino-1,2,3,4-tetrahydro-naphthalenes are agonists of dopaminergic receptors and several studies about the structure-activity relationship have been carried out to determine the structural characteristics able to ensure the best dopaminergic activity and to avoid, at the same time, the undesired effects of dopamine.

An interesting review of these studies is collected in a paper published by H. E. Katerinopoulos and D. I. Schuster on Drugs of the Future, vol. 12(3), pages 223–253, (1987).

In spite of the various studies, however, the topology of dopaminergic receptors has not yet been explained and a series of receptor models has been proposed in the last ten years.

In the field of the compounds structurally related to dopamine and/or to 2-amino-1,2,3,4-tetrahydronaphthalene, some authors have found that the presence of a $C_3$–$C_4$ alkyl group on the amino function is one of the requirements for dopaminergic activity while the structural requirements of the second substituent on the amino group have not yet been found.

Nevertheless, there are several examples in literature showing how the structural features of the two substituents can be, in practice, extremely variable and how small changes of the molecule can affect the pharmacological activity both quantitatively and qualitatively in a relevant manner.

Among the most significant examples the following are cited. European patent application no. 72061 (Fisons PLC) describes, among the others, dopamines and aminotetrahydronaphthalenes having a mono- or di-substituted portion of formula $$-\underset{R^1}{N}-CH_2-X-CH_2-\underset{R^2}{N}-D_2$$

wherein

X is a —$(CH_2)_n$— chain, optionally substituted by hydroxy; n is an integer between 1 and 7; $R_1$ and $R_2$, the same or different, are hydrogen, alkyl or phenyl; $D_2$ is hydrogen, alkyl, phenyl; alkyl substituted by one or more hydroxy, pyridyl, phenyl; alkyl substituted by phenyl substituted, in turn, by halogen, alkyl, amino, alkoxy or nitro; or $D_2$ may be an optionally mono- or di-hydroxy substituted phenylethyl or tetrahydronaphthyl moiety.

Among the compounds described in European patent application no. 72061, the compound of formula whose International non-proprietary name is dopexamine (The Merck Index—XI ed., No. 3418, page 538) is the only compound, as far as we know, which has been developed and used in the acute treatment of failure.

It is significant that dopexamine, notwithstanding it was selected among the several compounds described and exemplified in European patent application no. 72061, is an agonist of dopaminergic receptors less active than dopamine and, like dopamine itself, it is not absorbed when administered by oral route [A. Fitton and P. Benfield, Drugs, 39(2), 308–330, (1990)].

European patent application no. 142283 (Fisons PLC) describes a class of compounds which are analogs of dopexamine and in which the amino group of the dopamine moiety is still secondary.

In literature, there are several compounds with a catecholamine structure having the aim of keeping the favourable properties of dopexamine, also when administered by oral route, or of increasing the selectivity towards the dopaminergic receptors.

Among these, those described in European patent application No. 321968 (SIMES Società Italiana Medicinali e Sintetici S.p.A.) having the following general formula:

wherein

R and $R_1$, the same or different, are hydrogen or acyl deriving from an aliphatic, aromatic or heteroaromatic carboxylic acid, from a carbonic or carbamic acid or from a phosphoric acid; n and p are integer numbers selected among 0 and 1; m is an integer number selected among 1, 2, 3 and 4 so that n+p=1 and m+n is 2, 3 or 4; $R_2$ and $R_3$, the same or different, are hydrogen, halogen, alkyl or alkoxy;

are particularly interesting.

These compounds are agonists of $D_1$ and $D_2$ dopaminergic receptors, show contemporaneously an $\alpha_1$-antagonist effect, do not interact with other receptor systems, but in order to be active by oral administration they have to be transformed into suitable pro-drugs. The compounds described in the International patent application WO 93/19036 (Zambon Group S.p.A.), which are dopaminergic agonists more potent than dopamine and not selective towards any specific receptor sub-type, which do not interact with other receptor systems and which, at the same time, do not show either the side effect or the therapeutically disadvantageous aspects of dopamine, are still more interesting.

The compounds described in the above cited International patent application have the following general formula:

wherein $R_1$ and $R_2$, the same or different, are hydrogen atoms or OY' groups;

Y and Y', the same or different, are hydrogen atoms or acyl groups deriving from an aliphatic, aromatic or heteroaromatic carboxylic acid, from a carbonic or carbamic acid or from a phosphoric acid; m is 1 or 2;

n is an integer number among 3 and 7; $R_3$ is hydrogen or $C_1$–$C_4$ alkyl; $R_4$ and $R_5$, the same or different, are hydrogen, halogen, $C_1$–$C_3$ alkyl or alkoxy.

The International patent application WO 95/07885 (Zambon Group S.p.A.), published on 23 Mar. 1995 claiming the Italian priority MI93A001973 of 14 Sep. 1993, describes dopaminergic agonists of formula

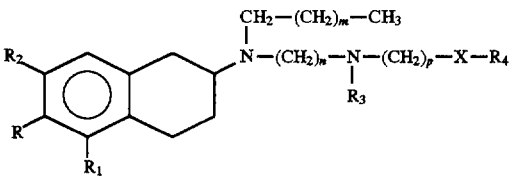

wherein

R is a hydrogen atom or an OY group; $R_1$ is a hydrogen atom or an OY' group; $R_2$ is a hydrogen atom or an OY" groups; provided that at least one among R, $R_1$ and $R_2$ is hydrogen but R, $R_1$ and $R_2$ are not contemporaneously hydrogen atoms and $R_1$ and $R_2$ are not contemporaneously OY' or OY" groups respectively; Y, Y' and Y", the same or different, are a hydrogen atom or an acyl group deriving from an optionally substituted aliphatic, aromatic or heteroaromatic carboxylic acid, from an optionally substituted carbonic or carbamic acid or from a phosphoric acid; m is 1 or 2; n is an integer number among 3 and 8; p is an integer number among 2 and 4; $R_3$ is hydrogen or $C_1$–$C_4$ alkyl; $R_4$ is a phenyl optionally substituted by halogen, $C_1$–$C_3$ alkyl or alkoxy or a 5- or 6-membered heteroaryl containing one or more heteroatoms selected among oxygen, nitrogen and sulphur, optionally substituted by halogen, hydroxy, $C_1$–$C_3$ alkyl or alkoxy groups; X is $CH_2$, NH, S, SO, $SO_2$, CO, $CF_2$, O and, when $R_4$ is a 5- or 6-membered heteroaryl, X can be also a single bond; provided that when X is O, $R_4$ is different from phenyl or pyridyl.

We have now found agonists of dopaminergic receptors more potent than dopamine and than the other above described known compounds, which are substantially devoid of interaction with the other receptor systems and which can be absorbed by oral route with a long duration of action.

Therefore, object of the present invention are compounds of formula

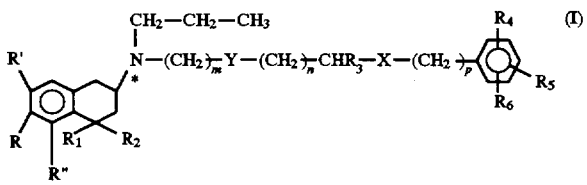

wherein m is an integer number selected among 4, 5, 6, 7 and 8;

R, R' and R" are hydrogen atoms or OH groups, provided that at least one among R, R' and R" is a hydrogen atom but R, R' and R" are not all contemporaneously hydrogen atoms and R' and R" are not both contemporaneously OH groups;

or one of R' and R" is a NHCHO, $NHCH_3$, $NHSO_2CH_3$, $CH_2OH$ or $CH_3$ group and the other is hydrogen;

$R_1$ and $R_2$, the same or different, are hydrogen atoms, $C_1$–$C_3$ alkyl groups or, together with the carbon atom to which they are bonded, form a cyclopropyl;

n is an integer number selected among 0, 1, 2, 3 and 4;

p is an integer number selected between 0 and 1;

$R_3$ is a hydrogen atom or a $C_1$–$C_4$ alkyl group;

Y is S, O, $N(R_7)CO$, $CO(R_7)N$ or $N(R_7)$;

X is $N(R_8)$, O, S, SO, $SO_2$, CO or a single bond;

$R_4$, $R_5$ and $R_6$, the same or different, are hydrogen, OH, halogen, $C_1$–$C_4$ alkyl, $C_1$–$C_4$ alkoxy, nitro, $C_1$–$C_4$ alkylthio, $NH_2$, mono- or di-$C_1$–$C_4$ alkylamino, SH, $C_1$–$C_4$ alkylsulphonyl, $C_1$–$C_4$ alkoxycarbonyl, NHCHO, $C_1$–$C_4$ alkylcarbonylamino, $NHCONH_2$, $C_1$–$C_4$ alkylsulphonylamino, $C_1$–$C_4$ alkylaminosulphonyl, $SO_2NH_2$, $NHSO_2NH_2$, COOH, $SO_3H$, $CONH_2$, $CH_2OH$ or phenyl; or $R_4$ and $R_5$, in ortho position one with respect to the other, together form an optionally unsaturated chain made by 3 or 4 groups selected among $CR'''R^{IV}$, CO, S, O and $NR^V$, wherein R''' is a hydrogen atom or a $C_1$–$C_4$ alkyl group, $R^{IV}$ is a hydrogen atom, a $C_1$–$C_4$ alkyl group or an amino group and and $R^V$ is a hydrogen atom or a $C_1$–$C_4$ alkyl group; or R''' together with a vicinal R''' or $R^V$ constitutes a single bond or $R^V$ together with a vicinal R''' or $R^V$ constitutes a single bond;

$R_7$ is a hydrogen atom or a $C_1$–$C_4$ alkyl group;

$R_8$ is a hydrogen atom; or $R_7$ and $R_8$ together form a —$CH_2$— or —$CH_2$—$CH_2$— chain; or $R_4$, when in ortho position with respect to X, constitutes a single bond or form a —$CH_2$— or —$CH_2$—$CH_2$— chain with $R_7$; or when X=O $R_4$, when in ortho position with respect to X, can form a —$CH_2$—O— chain with $R_3$;

the asterisk marks an asymmetric carbon atom;

provided that when p=1, X is an $N(R_8)$ group; and provided that when R and R' or R" are OH groups, $R_1$ and $R_2$ are hydrogen atoms and a) when Y is $N(R_7)$, $R_7$ is hydrogen or alkyl and $R_3$ is hydrogen, at least one among $R_4$, $R_5$ and $R_6$ is different from hydrogen, halogen, $C_1$–$C_4$ alkyl and $C_1$–$C_4$ alkoxy;

b) when Y is $N(R_7)$, $R_7$ is hydrogen or alkyl, $R_3$ is hydrogen and X is a simple bond, at least one among $R_4$, $R_5$ and $R_6$ is different from hydrogen, halogen, $NH_2$, $C_1$–$C_2$ alkyl, $C_1$–$C_4$ alkoxy and nitro;

c) when Y is $N(R_7)$, $R_7$ is hydrogen or alkyl, n is 1, $R_3$ is hydrogen and X is a simple bond, at least one among $R_4$, $R_5$ and $R_6$ is different from hydrogen and from OH;

and pharmaceutically acceptable salts thereof.

Proviso a) excludes from formula I the compounds comprised in the above cited International patent applications WO 93/19036 and WO 95/07885.

Provisos b) and c) exclude from formula I the compounds comprised in the above cited European patent application No. 72061.

The compounds of formula I have at least an asymmetric center, marked by an asterisk, and they may be in the form of stereoisomers. Object of the present invention are the compounds of formula I in the form of stereoisomeric mixtures as well as in the form of single stereoisomers.

The compounds of formula I are agonists of dopaminergic receptors active also by oral route and with long duration of action and they are useful in therapy in cardiovascular field, in particular for the treatment of arterial hypertension and heart failure, of renal failure, in the treatment of peripheral arteriopathies, of cerebrovascular insufficiencies and of ischemic cardiopathy.

With the term halogen atom we intend a fluorine, chlorine, bromine or iodine atom.

Specific examples of alkyl or alkoxy groups are methyl, ethyl, n.propyl, i.propyl, n.butyl, i.butyl, sec.butyl, t.butyl, methoxy, ethoxy, n.propoxy, i.propoxy, n.butoxy and i.butoxy.

Specific examples of optionally unsaturated chains made by 3 or 4 groups selected among $CR'''R^{IV}$, CO, S, O and $NR^V$ are the following: —O—CHR'''—O—, —S—CO—$NR^V$—, —CHR'''—CO—$NR^V$—, —S—$CR^{IV}$=N—, O—CO—$NR^V$—, —CO—$NR^V$—$NR^V$—, $NR^V$—CO—$NR^V$—.

Preferred compounds of formula I are the compounds wherein R' is a hydrogen atom, R and R" are OH groups and the carbon atom marked by an asterisk has S configuration.

Still more preferred compounds are the compounds wherein R', $R_1$ and $R_2$ are hydrogen atoms, R and R" are OH groups, m is 6 and the carbon atom marked by an asterisk has S configuration.

Among the meanings of the substituents $R_4$, $R_5$ and $R_6$, the preferred are hydrogen, OH, methoxy, methyl, nitro, chloro, methylsulphonyl, $NH_2$, $SO_2NH_2$, methylsulphonylamino, $NH_2CONH_2$, methoxycarbonyl, acetylamino, $CONH_2$, $CH_2OH$, $SO_3H$ and methylenedioxy or, when $R^4$ and $R^5$ in ortho position one with respect to the other form a chain, a group of formula —S—CO—$NR^V$— wherein $R^V$ is a hydrogen atom.

Specific examples of compounds of formula I are:

(S)-N-propyl-N-[6-[(1,4-benzodioxan-2-yl)methylamino] hexyl]-5,6-dihydroxy-1,2,3,4-tetrahydro-2-naphthylamine (S)-N-propyl-N-[6-[2-(3-methylsulphonylphenyl) ethylamino]hexyl]-5,6-dihydroxy-1,2,3,4-tetrahydro-2-naphthylamine (S)-N-propyl-N-[6-[2-(3,4-methylendioxyphenyl) ethylamino]hexyl]-5,6-dihydroxy-1,2,3,4-tetrahydro-2-naphthylamine (S)-N-propyl-N-(5,6-dihydroxy-1,2,3,4-tetrahydro-2-naphthyl)-N'-methyl-N'-[2-(2-oxo-3H-1,3-benzothiazol-6-yl)ethyl]-1,6-hexanediamine (S)-N-propyl-N-[6-[4-(2-methoxyphenyl)piperazin-1-yl] hexyl]-5,6-dihydroxy-1,2,3,4-tetrahydro-2-naphthylamine (R)-N-propyl-N-[6-[2-(2-oxo-3H-1,3-benzothiazol-6-yl) ethylamino]hexyl]-6-hydroxy-7-formylamino-1,2,3,4-tetrahydro-2-naphthylamine (S)-N-propyl-N-[6-[2-(2-nitrophenoxy)ethylamino]hexyl]-5,6-dihydroxy-1,2,3,4-tetrahydro-2-naphthylamine (R)-N-propyl-N-[6-[2-(3-chloro-4-hydroxyphenyl) ethylamino]hexyl]-6-hydroxy-7-formylamino-1,2,3,4-tetrahydro-2-naphthylamine (S)-N-propyl-N-[6-[2-(4-nitrophenoxy)ethylamino]hexyl]-5,6-dihydroxy- 1,2,3,4-tetrahydro-2-naphthylamine (R)-N-propyl-N-[6-(2-phenylethylamino)hexyl]-6-hydroxy-7-formylamino-1,2,3,4-tetrahydro-2-naphthylamine (S)-N-propyl-N-[6-[2-(4-methylsulphonylphenoxy) ethylamino]hexyl]-5,6-dihydroxy-1,2,3,4-tetrahydro-2-naphthylamine (R)-N-propyl-N-[6-[2-(4-methylsulphonylphenyl) ethylamino]hexyl]-6-hydroxy-7-formylamino-1,2,3,4-tetrahydro-2-naphthylamine (S)-N-propyl-N-[6-[(2-methoxyphenoxy)acetylamino] hexyl]-5,6-dihydroxy-1,2,3,4-tetrahydro-2-naphthylamine (S)-N-propyl-N-[7-[2-(2-oxo-3H-1,3-benzothiazol-6-yl) ethylamino]heptyl]-5,6-dihydroxy-1,2,3,4-tetrahydro-2-naphthylamine (S)-N-propyl-N-[6-[2-(4-hydroxyphenylthio)ethylamino] hexyl]-5,6-dihydroxy-1,2,3,4-tetrahydro-2-naphthylamine (S)-N-propyl-N-[5-[2-(2-oxo-3H-1,3-benzothiazol-6-yl) ethylamino]pentyl]-5,6-dihydroxy-1,2,3,4-tetrahydro-2-naphthylamine (S)-N-propyl-N-[6-[3-(4-hydroxyphenyl)propylamino] hexyl]-5,6-dihydroxy-1,2,3,4-tetrahydro-2-naphthylamine (S)-N-propyl-N-[6-[2-(4-formylaminophenyl)ethylamino] hexyl]-5,6-dihydroxy-1,2,3,4-tetrahydro-2-naphthylamine (S)-N-propyl-N-[6-(6,7-dihydroxy-1,2,3,4-tetrahydroisoquinolin-2-yl)hexyl]-5,6-dihydroxy-1,2,3,4-tetrahydro-2-naphthylamine (S)-N-propyl-N-[5-[2-(2,3-dihydro-2-oxo-3-methyl-1,3-benzothiazol-6-yl)ethylamino]hexyl]-5,6-dihydroxy-1,2,3,4-tetrahydro-2-naphthylamine (S)-N-propyl-N-[6-[2-(3-chloro-4-hydroxyphenyl) ethylamino]hexyl]-5,6-dihydroxy-1,2,3,4-tetrahydro-2-naphthylamine (S)-N-propyl-N-[6-oxo-6-[2-(2-oxo-3H-1,3-benzothiazol-6-yl)ethylamino]hexyl]-5,6-dihydroxy-1,2,3,4-tetrahydro-2-naphthylamine (S)-N-propyl-N-[6-[2-(3-nitro-4-hydroxyphenyl) ethylamino]hexyl]-5,6-dihydroxy- 1,2,3,4-tetrahydro-2-naphthylamine (R)-N-propyl-N-[6-[2-(4-methylsulphonylphenyl) ethylamino]hexyl]-6,7-dihydroxy-1,2,3,4-tetrahydro-2-naphthylamine (S)-N-propyl-N-[6-[3-(3,4-dihydroxyphenyl)propylamino] hexyl]-5,6-dihydroxy-1,2,3,4-tetrahydro-2-naphthylamine (S)-N-propyl-N-[6-[2-(2,3-dihydro-3-oxo-1H-indazol-5-yl) ethylamino]hexyl]-5,6-dihydroxy-1,2,3,4-tetrahydro-2-naphthylamine (S)-N-propyl-N-[6-[2-(3-methyl-4-hydroxyphenyl) ethylamino]hexyl]-5,6-dihydroxy-1,2,3,4-tetrahydro-2-naphthylamine (S)-N-propyl-N-[6-[2-(2,3-dihydro-2-oxo-1H-benzimidazol-5-yl)ethylamino]hexyl]-5,6-dihydroxy-1,2,3,4-tetrahydro-2-naphthylamine (S)-N-propyl-N-[6-[4-(4-hydroxyphenylmethyl)piperazin-1-yl]hexyl]-5,6-dihydroxy-1,2,3,4-tetrahydro-2-naphthylamine (S)-N-propyl-N-[6-[2-(2,3-dihydro-2-oxo-3H-benzoxazol-6-yl)ethylamino]hexyl]-5,6-dihydroxy-1,2,3,4-tetrahydro-2-naphthylamine (S)-N-propyl-N-[6-[3-(2-hydroxyphenyl)propylamino] hexyl]-5,6-dihydroxy-1,2,3,4-tetrahydro-2-naphthylamine (S)-N-propyl-N-[6-[2-(4-aminophenyl)ethylamino]hexyl]-5,6-dihydroxy-1,2,3,4-tetrahydro-2-naphthylamine (S)-N-propyl-N-[6-[2-(3,5-dihydroxy-4-methylphenyl) ethylamino]hexyl]-5,6-dihydroxy-1,2,3,4-tetrahydro-2-naphthylamine (S)-N-propyl-N-[6-(2-phenylethylamino)hexyl]-6-hydroxy-5-hydroxymethyl-1,2,3,4-tetrahydro-2-naphthylamine (S)-N-propyl-N-[6-[2-(2-oxo-3H-1,3-benzothiazol-6-yl) ethylamino]hexyl]-5,6-dihydroxy-1,2,3,4-tetrahydro-2-naphthylamine (S)-N-propyl-N-[6-(2-phenylethylamino)hexyl]-5-formylamino-6-hydroxy-1,2,3,4-tetrahydro-2-naphthylamine (S)-N-propyl-N-[6-[2-(2-oxo-3H-1,3-benzothiazol-5-yl) ethylamino]hexyl]-5,6-dihydroxy-1,2,3,4-tetrahydro-2-naphthylamine (S)-N-propyl-N-[6-(2-phenylethylamino)hexyl]-6-hydroxy-5-methylsulphonylamino-1,2,3,4-tetrahydro-2-naphthylamine (S)-N-propyl-N-[6-[2-(2-oxo-3H-1,3-benzothiazol-6-yl)ethylamino]hexyl]-5-hydroxy-1,2,3,4-tetrahydro-2-naphthylamine (S)-N-propyl-N-[6-(2-phenylethylamino)hexyl]-5,6-dihydroxy-4-methyl-1,2,3,4-tetrahydro-2-naphthylamine (S)-N-propyl-N-[6-[2-(3-chloro-5-hydroxyphenyl)ethylamino]hexyl]-5,6-dihydroxy-1,2,3,4-tetrahydro-2-naphthylamine (S)-N-propyl-N-[6-(2-phenylethylamino)hexyl]-6-hydroxy-5-methyl-1,2,3,4-tetrahydro-2-naphthylamine (S)-N-propyl-N-[6-[2-(4-methylsulphonylphenyl)ethylamino]hexyl]-5,6-dihydroxy-1,2,3,4-tetrahydro-2-naphthylamine (S)-N-propyl-N-[6-(2-phenylethylamino)hexyl]-6-hydroxy-5-methylamino-1,2,3,4-tetrahydro-2-naphthylamine (S)-N-propyl-N-[6-(2,3-dihydro-indol-1-yl)hexyl]-5,6-dihydroxy-1,2,3,4-tetrahydro-2-naphthylamine (S)-N-propyl-N-[6-[2-(3-chloro-4-hydroxyphenyl)ethylamino)hexyl]-6-hydroxy-5-hydroxymethyl-1,2,3,4-tetrahydro-2-naphthylamine (S)-N-propyl-N-[6-[2-(4-hydroxyphenoxy)ethylamino]hexyl]-5,6-dihydroxy-1,2,3,4-tetrahydro-2-naphthylamine (S)-N-propyl-N-[6-[2-(3-chloro-4-hydroxyphenyl)ethylamino)hexyl]-5-formylamino-6-hydroxy-1,2,3,4-tetrahydro-2-naphthylamine (S)-N-propyl-N-[6-[2-(3,4-dihydroxyphenyl)ethoxy]hexyl]-5,6-dihydroxy-1,2,3,4-tetrahydro-2-naphthylamine (S)-N-propyl-N-[6-[2-(3-chloro-4-hydroxyphenyl)ethylamino)hexyl]-5-hydroxy-6-methylsulphonylamino-1,2,3,4-tetrahydro-2-naphthylamine (S)-N-propyl-N-[6-[2-(3-methoxy-4-hydroxyphenyl)ethylamino]hexyl]-5,6-dihydroxy-1,2,3,4-tetrahydro-2-naphthylamine (S)-N-propyl-N-[6-[2-(3-chloro-4-hydroxyphenyl)ethylamino)hexyl]- 5,6-dihydroxy-4-methyl-1,2,3,4-tetrahydro-2-naphthylamine (S)-N-propyl-N-[6-[2-(3-hydroxy-4-methoxyphenyl)ethylamino]hexyl]-5,6-dihydroxy-1,2,3,4-tetrahydro-2-naphthylamine (S)-N-propyl-N-[6-[2-(3-chloro-4-hydroxyphenyl)ethylamino)hexyl]-6-hydroxy-5-methyl-1,2,3,4-tetrahydro-2-naphthylamine (S)-N-propyl-N-[6-[2-(3,4-dihydroxyphenyl)ethylthio]hexyl]-5,6-dihydroxy-1,2,3,4-tetrahydro-2-naphthylamine (S)-N-propyl-N-[6-[2-(3-chloro-4-hydroxyphenyl)ethylamino)hexyl]-6-hydroxy-5-methylamino-1,2,3,4-tetrahydro-2-naphthylamine (S)-N-propyl-N-[6-[2-(3-amino-4-hydroxyphenyl)ethylamino]hexyl]-5,6-dihydroxy-1,2,3,4-tetrahydro-2-naphthylamine (S)-N-propyl-N-[6-[2-(4-methylsulphonylphenyl)ethylamino)hexyl]-6-hydroxy-5-hydroxymethyl-1,2,3,4-tetrahydro-2-naphthylamine (S)-N-propyl-N-[6-[2-(4-sulphamoylphenyl)ethylamino]hexyl]-5,6-dihydroxy-1,2,3,4-tetrahydro-2-naphthylamine (S)-N-propyl-N-[6-[2-(4-methylsulphonylphenyl)ethylamino)hexyl]-5-formylamino-6-hydroxy-1,2,3,4-tetrahydro-2-naphthylamine (S)-N-propyl-N-[6-[2-(4-methylsulphonylaminophenyl)ethylamino]hexyl]-5,6-dihydroxy-1,2,3,4-tetrahydro-2-naphthylamine (S)-N-propyl-N-[6-[2-(4-methylsulphonylphenyl)ethylamino)hexyl]-6-hydroxy-5-methylsulphonylamino-1,2,3,4-tetrahydro-2-naphthylamine (S)-N-propyl-N-[6-[2-(4-aminocarbonylaminophenyl)ethylamino]hexyl]-5,6-dihydroxy-1,2,3,4-tetrahydro-2-naphthylamine (S)-N-propyl-N-[6-[2-(4-methylsulphonylphenyl)ethylamino)hexyl]-5,6-dihydroxy-4-methyl-1,2,3,4-tetrahydro-2-naphthylamine (S)-N-propyl-N-[6-[2-(4-acetylaminophenyl)ethylamino]hexyl]-5,6-dihydroxy-1,2,3,4-tetrahydro-2-naphthylamine (S)-N-propyl-N-[6-[2-(4-methylsulphonylphenyl)ethylamino)hexyl]-6-hydroxy-5-methyl-1,2,3,4-tetrahydro-2-naphthylamine (S)-N-propyl-N-[6-[(3,4-dihydroxyphenyl)acetylamino]hexyl]-5,6-dihydroxy-1,2,3,4-tetrahydro-2-naphthylamine (S)-N-propyl-N-[6-[2-(4-methylsulphonylphenyl)ethylamino)hexyl]-6-hydroxy-5-methylamino-1,2,3,4-tetrahydro-2-naphthylamine (S)-N-propyl-N-[6-[2-(4-methoxycarbonylphenyl)ethylamino]hexyl]-5,6-dihydroxy-1,2,3,4-tetrahydro-2-naphthylamine (S)-N-propyl-N-[6-[2-(4-hydroxymethylphenyl)ethylamino]hexyl]-5,6-dihydroxy-1,2,3,4-tetrahydro-2-naphthylamine (S)-N-propyl-N-[6-[2-(4-carbamoylphenyl)ethylamino]hexyl]-5,6-dihydroxy-1,2,3,4-tetrahydro-2-naphthylamine (S)-N-propyl-N-[6-[2-(4-carboxyphenyl)ethylamino]hexyl]-5,6-dihydroxy-1,2,3,4-tetrahydro-2-naphthylamine (S)-N-propyl-N-[6-[2-(4-sulphophenyl)ethylamino]hexyl]-5,6-dihydroxy-1,2,3,4-tetrahydro-2-naphthylamine (S)-N-propyl-N-[6-[2-(2-amino-1,3-benzothiazol-6-yl)ethylamino]hexyl]-5,6-dihydroxy-1,2,3,4-tetrahydro-2-naphthylamine Pharmaceutically acceptable salts of the compounds of formula I are the salts with organic and inorganic acids such as, for example, hydrochloric, hydrobromic, hydroiodic, nitric, sulphuric, phosphoric, acetic, benzoic, maleic, fumaric, succinic, tartaric, citric, aspartic, methansulphonic and 3,7-di-tert.butylnaphthalen-1,5-disulphonic acid (dibudinic acid).

The preparation of the compounds of formula I can be carried out according to the synthetic method described herein after.

The method comprises the reaction between a compound of formula

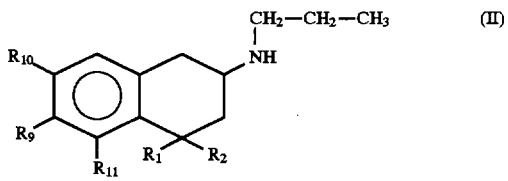

wherein $R_1$ and $R_2$ have the already reported meanings;

$R_9$, $R_{10}$ and $R_{11}$, are hydrogen atoms or OZ groups wherein Z is a hydrogen atom or a protective group selected, for example, among methyl, benzyl, benzoyl and 4-methoxybenzoyl, provided that at least one among $R_9$, $R_{10}$ and $R_{11}$ is a hydrogen atom but $R_9$, $R_{10}$ and $R_{11}$ are not all contemporaneously hydrogen atoms and $R_{10}$ and $R_{11}$ are not both contemporaneously OZ groups; or one of $R_{10}$ and $R_{11}$ is an NHCHO, $NHCH_3$, $NHSO_2CH_3$, $CH_2OH$ or $CH_3$ group and the other is hydrogen;

and an acid of formula

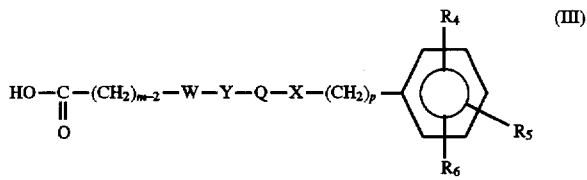

wherein m, p, $R_4$, $R_5$, $R_6$, X and Y have the already reported meanings; W is a $CH_2$ or CO group; Q is a group of formula $CO-(CH_2)_{n-1}-CHR_3$ wherein $R_3$ has the already reported meanings, when n is 1, 2, 3 or 4; or Q is a $CHR_3$ or CO group, wherein $R_3$ has the already reported meanings, when n is 0;

or a reactive derivative thereof such as an acyl halide or a mixed anhydride which can optionally be prepared in situ, in an inert solvent and in the presence of a base such as an alkaline carbonate or bicarbonate or a tertiary amine, in order to obtain the intermediate compounds of formula

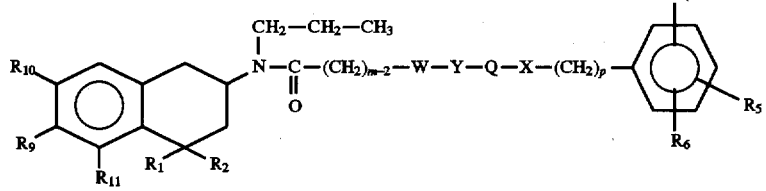

wherein m, p, W, Y, Q, X, $R_1$, $R_2$, $R_4$, $R_5$, $R_6$, $R_9$, $R_{10}$ and $R_{11}$ have the already reported meanings;

and their reduction, preceded or followed by the optional deprotection of the hydroxy groups, in order to obtain the compounds of formula I.

The reduction of the compounds of formula IV can be carried out with electrophile reducing agents, in particular with diborane optionally complexed with dimethylsulphide, tetrahydrofuran, aliphatic amines such as triethylamine or aromatic amines such as N,N-diethylaniline or pyridine.

Alternatively, the reduction can be carried out with nucleophile reducing agents such as metal hydrides, for example lithium aluminum hydride.

The reduction reaction is carried out in a suitable solvent such as for example tetrahydrofuran, diethylether or 1,2-dimethoxyethane. The optional deprotection of the hydroxy groups is carried out according to conventional techniques such as hydrolysis or hydrogenolysis.

The compounds of formula II are known or easily prepared according to known methods (British patent no 1509454—The Wellcome Foundation Ltd.).

Also the compounds of formula III are known or easily prepared according to conventional methods.

Alternatively, the compounds of formula I wherein Y is a $N(R_7)$ can be prepared following a different sequence.

At first it is carried out the condensation reaction between a compound of formula II and a suitable reactive derivative of an acid of formula

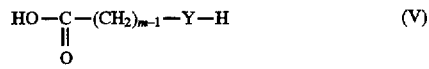

wherein Y is an $N(R_7)$ group; m and $R_7$ have the already reported meanings;

followed by the optional reduction according to what already reported, in order to obtain the intermediate of formula

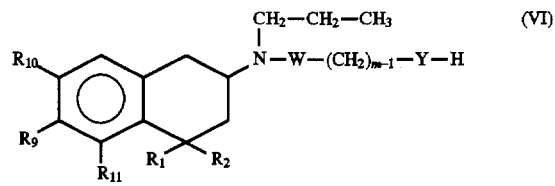

wherein Y is an $N(R_7)$ group; m, W, $R_1$, $R_2$, $R_7$, $R_9$, $R_{10}$ and $R_{11}$ have the already reported meanings.

The intermediate of formula VI is then reacted with a suitable reactive derivative of an acid of formula

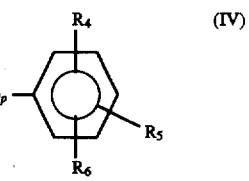

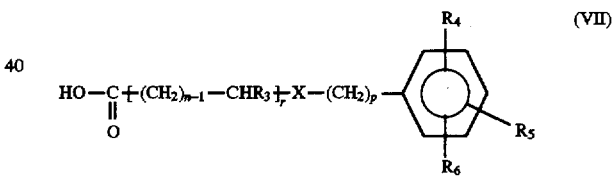

wherein n, p, $R_3$, $R_4$, $R_5$, $R_6$ and X have the already reported meanings; r is 0 or 1;

obtaining the corresponding intermediates of formula IV.

The subsequent reduction, preceded or followed by the optional deprotection of the hydroxy groups, gives the compounds of formula I wherein Y is a $N(R_7)$ group, object of the present invention.

A further alternative for the preparation of the compounds of formula I wherein Y is an $N(R_7)$ group consists in first reacting a compound of formula II with a suitable reactive derivative of a bicarboxylic acid of formula

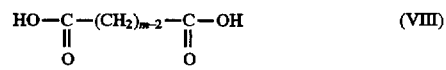

wherein m has the already reported meanings;

in order to obtain an intermediate of formula

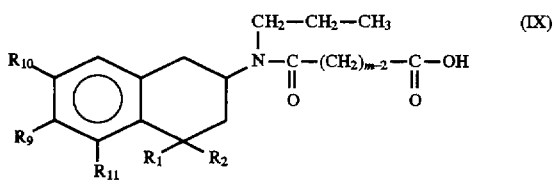

wherein m, $R_1$, $R_2$, $R_9$, $R_{10}$ and $R_{11}$ have the already reported meanings.

The subsequent condensation with an amine of formula

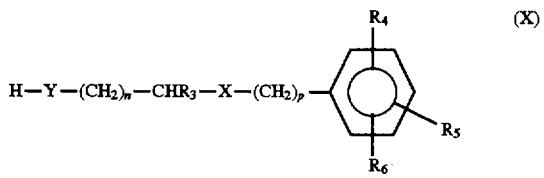

wherein Y is an $N(R_7)$ group; n, p, X, $R_3$, $R_4$, $R_5$, $R_6$ and $R_7$ have the already reported meanings;
gives the corresponding intermediates of formula IV.

The subsequent reduction, preceded or followed by the optional deprotection of the hydroxy groups, allows to obtain the compounds of formula I wherein Y is an $N(R_7)$ group, object of the present invention.

Some of the compounds of formula I, optionally protected, may also be used as intermediates for the synthesis of other compounds of formula I by transformation of certain functional groups present in the molecule.

Thus, for example, compounds of formula I wherein one or more of $R_4$, $R_5$ and $R_6$ is a nitro group or an alkoxycarbonyl group can be transformed into the corresponding compounds of formula I wherein one or more of $R_4$, $R_5$ and $R_6$ is an amino or carboxy group by reduction or hydrolysis respectively. In turn, compounds of formula I wherein one or more of $R_4$, $R_5$ and $R_6$ is an amino group or a carboxy group can be transformed into the corresponding compounds of formula I wherein one or more of $R_4$, $R_5$ and $R_6$ is an alkylcarbonylamino or $CH_2OH$ group by acylation or reduction respectively.

Analogously, the same transformation can be carried out on intermediates of formula IV.

The compounds of formula I in optically active form are obtained by optical separation or by stereospecific or stereoselective synthesis.

The preparation of salts of the compounds of formula I is carried out according to conventional methods.

The compounds of formula I are agonists of $D_1$ and $D_2$ dopaminergic receptors having more affinity than dopamine and than dopexamine as results from the in vitro binding tests (example 48).

Furthermore, their activity is at least comparable to that of the compounds described in the International patent application WO 93/19036.

The in vitro results have been confirmed also by functional studies on isolated tissues, which ate predictive of the in vivo activity, such as the Rabbit Splenic Artery (RSA) test and the Rabbit Ear Artery (REA) test (example 49).

The in vivo activity of the compounds of formula I, object of the present invention, has been evaluated by intravenous administration to rats (example 50).

The tests for interaction with the other receptor systems showed that the compounds of formula I do not significantly interact and then are endowed with high specificity.

The compounds of formula I resulted also to be inactive on the central nervous system after opal administration and this lack of effect is a further positive property generally not shared with the other compounds having a cathecolamine structure.

It is clear how these characteristics of selectivity and receptor specificity together with the lack of activity on the central nervous system make the compounds of formula I particularly suitable for the treatment of cardiovascular diseases and mainly in the antihypertensive therapy, in the therapy of hearth failure, of renal insufficiency, in the treatment of peripheral arteropathies, of cerebrovascular insufficiencies and of ischemic cardiopathy.

In addition to the already underlined higher pharmacologic activity, the feature which more characterizes the compounds of formula I, object of the invention is their absorbability by oral route and their long lasting activity.

As a consequence for the practical uses in therapy, the compounds of formula I can be administered by parenteral route as well as by enteral route so differing from dopamine and from dopexamine.

The therapeutic doses will be generally comprised between 5 mg and 1 g a day and between 1 and 300 mg by oral route for each single administration.

The pharmaceutical compositions containing a therapeutically effective amount of the compounds of formula I or of their pharmaceutically acceptable salts in admixture with a suitable carrier are, furthermore, object of the present invention.

The pharmaceutical compositions object of the invention may be liquid, suitable for enteral or parenteral administration, and, preferably, solid such as tablets, capsules, granulates, suitable for oral administration.

The preparation of the pharmaceutical compositions object of the invention can be carried out according to traditional techniques. Notwithstanding the compounds of formula I are active as such also when orally administered, in order to fulfill some specific therapeutic or pharmaceutical requirements it can be useful to transform them into the corresponding pro-drugs.

According to the techniques used in the field of phenol and cathecol derivatives, suitable pro-drugs are obtained by esterification of one or two hydroxy groups with pharmaceutically acceptable salts.

Specific examples of pro-drugs of the compounds of formula I are acetoxy derivatives, wherein the hydroxy groups are esterified with acetic acid, and mono- or di-phosphonates, wherein one or both hydroxy groups are esterified with phosphoric acid.

The compounds of formula I also when transformed into pro-drugs and in particular the compounds obtained by esterification of the phenol hydroxy groups or of one or both the cathecol hydroxy groups with pharmaceutically acceptable acids, as well as the pharmaceutical compositions which contain a compound of formula I in the form of a corresponding pro-drug, and in particular which contain a compound of formula I wherein the phenol hydroxy groups or of one or both the cathecol hydroxy groups are esterified with pharmaceutically acceptable acids are within the scope of the present invention.

In order to better illustrate the present invention the following examples are now given.

The chromatographic purifications were carried out on silica gel (230–400 mesh) columns.

The mass spectra, if not otherwise specified, were carried out under the following conditions: chemical ionization, isobutane, positive ions.

The following abbreviations were used: DMF for N,N-dimethylformamide, THF for tetrahydrofuran and DMSO for dimethylsulphoxide.

EXAMPLE 1

Preparation of 6-[(4-methoxyphenylthio)acetylamino] hexanoic acid (Intermediate 1)

DMF (50 µl) and thionyl chloride (1.8 g; 15.1 mmoles) were added to a solution of (4-methoxyphenylthio)acetic acid (2 g; 10.1 mmoles), prepared as described in J. Org. Chem., 56(18), 5346–8 (1991), in $CH_2Cl_2$ (20 ml) under stirring at room temperature.

After 1 hour the solvent was evaporated under reduced pressure and the resultant oil was dissolved in $CH_2Cl_2$ (3 ml).

The resultant solution and, contemporaneously, a 4N NaOH solution (3 ml) were added dropwise under vigorous stirring to a solution of 6-aminohexanoic acid (1.3 g; 9.9 mmoles) and NaOH (0.4 g; 10 mmoles) in water (5 ml).

The reaction mixture was kept under stirring at room temperature for 2 hours.

After separation of the phases, the aqueous phase was washed with $CH_2Cl_2$ (5 ml), acidified with HCl 37% up to pH 1 and then extracted with $CH_2Cl_2$ (20 ml).

The organic phase was dried on $Na_2SO_4$.

After cooling at 0° C. and filtration of the resultant solid, Intermediate 1 (2.4 g) was obtained.

$^1$H-NMR (200 MHz; DMSO-$d_6$): δ(ppm): 1.15–1.62 (m, 6H); 2.15 (t, 2H); 3.00 (m, 2H); 3.56 (s, 2H); 3.73 (s, 3H); 6.85–7.18 (m, 4H); 7.95 (bt, 1H).

Mass: 312 [M+1].

By working in a similar way the following compounds were prepared.

6-[(4-phenylmethoxyphenoxy)acetylamino]hexanoic acid (Intermediate 2) starting from (4-phenylmethoxyphenoxy) acetic acid, prepared as described in J. Med. Chem., 15(9), 940–4 (1972).

$^1$H-NMR (200 MHz; DMSO-$d_6$): δ(ppm): 1.10–1.56 (m, 6H); 2.17 (t, 2H); 3.07 (m, 2H); 4.36 (s, 2H); 5.02 (s, 2H); 6.82–6.98 (m, 4H); 7.24–7.45 (m, 5H); 8.01 (bt, 1H); 12.00 (bs, 1H).

Mass: 372 [M+1].

6-[3-(4-methoxyphenyl)propionylamino]hexanoic acid (Intermediate 3) starting from 3-(4-methoxyphenyl) propionic acid (Aldrich)

$^1$H-NMR (200 MHz; CDCl$_3$): δ(ppm): 1.15–1.67 (m, 6H); 2.30 (t, 2H); 2.41 (t, 2H); 2.87 (t, 2H); 3.18 (m, 2H); 3.76 (s, 3H); 5.43 (bt, 1H); 6.75–7.14 (m, 4H).

Mass: 294 [M+1].

6-[(3,4-methylendioxyphenyl)acetylamino]hexanoic acid (Intermediate 4) starting from (3,4-methylendioxyphenyl) acetic acid (Aldrich)

$^1$H-NMR (200 MHz; CDCl$_3$): δ(ppm): 1.17–1.68 (m, 6H); 2.31 (t, 2H); 3.19 (m, 2H); 3.46 (s, 2H); 5.47 (bt, 1H); 5.95 (s, 2H); 6.62–6.80 (m, 3H).

Mass: 294 [M+1].

6-[(1,4-benzodioxan-2-yl)carbonylamino]hexanoic acid (Intermediate 5) starting from 2-carboxy-1,4-benzodioxane, prepared as described in J. Am. Chem. Soc., 77, 5373 (1955)

$^1$H-NMR (200 MHz; DMSO-$d_6$): δ(ppm): 1.21–1.69 (m, 6H); 2.32 (t, 2H); 3.31 (m, 2H); 4.16 (dd, 1H); 4.49 (dd, 1H); 4.66 (dd, 1H); 6.57 (bt, 1H); 6.81–6.98 (m, 4H).

Mass: 294 [M+1].

6-[3-(2-methoxyphenyl)propionylamino]hexanoic acid (Intermediate 6) starting from 3-(2-methoxyphenyl) propionic acid (Aldrich)

$^1$H-NMR (300 MHz; CDCl$_3$): δ(ppm): 1.15–1.67 (m, 6H); 2.30 (t, 2H); 2.46 (t, 2H); 2.91 (t, 2H); 3.18 (m, 2H); 3.81 (s, 3H); 5.55 (bt, 1H) 6.79–7.25 (m, 4H).

Mass: 294 [M+1].

6-[(2-nitrophenoxy)acetylamino]hexanoic acid (Intermediate 7) starting from (2-nitrophenoxy)acetic acid, prepared as described in J. Med. Chem., 27, 967–78 (1984)

$^1$H-NMR (200 MHz; CDCl$_3$): δ(ppm): 1.30–1.74 (m, 6H); 2.33 (t, 2H); 3.30–3.42 (m, 2H); 4.62 (s, 2H); 7.27 (bt, 1H); 7.00–8.04 (m, 4H).

Mass: 311 [M+1].

6-[(4-nitrophenoxy)acetylamino]hexanoic acid (Intermediate 8) starting from (4-nitrophenoxy)acetic acid, prepared as described in J. Med. Chem., 27, 967–78 (1984)

$^1$H-NMR (200 MHz; DMSO-$d_6$): δ(ppm): 1.10–1.55 (m, 6H); 2.16 (t, 2H); 3.09 (m, 2H); 4.62 (s, 2H); 7.13 (m, 2H); 8.14–8.26 (m, 3H).

Mass: 311 [M+1].

6-[(4-methylsulphonylphenoxy)acetylamino]hexanoic acid (Intermediate 9) starting from (4-methylsulphonylphenoxy) acetic acid, prepared as described in J. Med. Chem., 27, 967–78 (1984)

$^1$H-NMR (200 MHz; DMSO-$d_6$): δ(ppm): 1.12–1.56 (m, 6H); 2.17 (t, 2H); 3.02–3.15 (m, 2H); 3.14 (s, 3H); 4.59 (s, 2H); 7.13 (m, 2H); 7.85 (m, 2H); 8.16 (bt, 1H); 12.01 (bs, 1H).

Mass: 344 [M+1].

6-[(4-nitrophenyl)acetylamino]hexanoic acid (Intermediate 10) starting from (4-nitrophenyl)acetic acid (Aldrich)

$^1$H-NMR (200 MHz; DMSO-$d_6$): δ(ppm): 1.12–1.57 (m, 6H); 2.17 (t, 2H); 2.96–3.10 (m, 2H); 3.55 (s, 2H); 7.47–7.57 (m, 2H); 8.07–8.20 (m, 3H).

Mass: 295 [M+1].

EXAMPLE 2

Preparation of 6-(6,7-dimethoxy-1,2,3,4-tetrahydro-isoquinolin-2-yl)-6-oxo-hexanoic acid (Intermediate 11)

A solution of hexandioic acid chloride monomethyl ester (3.6 g; 20.2 mmoles) in $CH_2Cl_2$ (10 ml) was added to a solution of 6,7-dimethoxy-1,2,3,4-tetrahydroisoquinoline hydrochloride (3.1 g; 13.5 mmoles) (Aldrich) and triethylamine (3.7 g; 37.1 mmoles) in $CH_2Cl_2$ (50 ml), under stirring at room temperature.

After 2 hours water (50 ml) was added and the phases were separated.

The organic phase was washed with a 0.2N HCl aqueous solution and then with a NaCl saturated solution.

After drying on $Na_2SO_4$ and evaporation to dryness under reduced pressure, the residue was dissolved in methanol (10 ml).

A solution of NaOH (1.1 g; 27.5 mmoles) in water (5 ml) was added dropwise to the resultant solution, under stirring at room temperature, and the reaction mixture was kept under stirring for 2 hours.

After evaporation of methanol under reduced pressure, water (10 ml), $CH_2Cl_2$ (20 ml) and HCl 37% up to pH 1 were added.

After separation of the phases, the aqueous phase was extracted again with $CH_2Cl_2$ (20 ml).

The collected organic phases were dried on $Na_2SO_4$ obtaining, after evaporation of the solvent, Intermediate 11 (3.6 g) as an oil.

$^1$H-NMR (200 MHz; CDCl$_3$): δ(ppm): 1.54–1.80 (m, 4H); 2.27–2.49 (m, 4H); 2.69–2.85 (m, 2H); 3.65 and 3.79 (2t, 2H); 3.84 (s, 6H); 4.53 and 4.64 (2s, 2H); 6.58 and 6.61 (2s, 2H).

Mass: 322 [M+1].

By working in a similar way the following compounds were prepared.

6-[4-(2-methoxyphenyl)-piperazin-1-yl]-6-oxo-hexanoic acid (Intermediate 12) starting from 4-(2-methoxyphenyl)piperazine (Aldrich)

$^1$H-NMR (200 MHz; DMSO-d$_6$): δ(ppm): 1.42–1.59 (m, 4H); 2.13–2.40 (m, 4H); 2.81–3.00 (m, 4H); 3.50–3.61 (m, 4H); 3.78 (s, 3H); 6.82–7.01 (m, 4H).

Mass (chemical ionization, methane, positive ions): 321 [M+1].

6-(2,3-dihydro-indol-1-yl)-6-oxo-hexanoic acid (Intermediate 13) starting from 2,3-dihydroindole (Aldrich)

$^1$H-NMR (200 MHz; CDCl$_3$): δ(ppm): 1.69–2.00 (m, 4H); 2.32–2.66 (m, 4H); 3.23 (t, 2H); 4.10 (t, 2H); 6.97–8.31 (m, 4H).

Mass: 248 [M+1].

EXAMPLE 3

Preparation of 6-[2-[3,4-di(phenylmethoxy)phenyl]ethoxy]hexanoic acid (Intermediate 14)

NaH (0.7 g 29.2 mmoles) was added, under nitrogen at room temperature, to a solution of 2-[3,4-di(phenylmethoxy)phenyl]ethanol (9 g; 26.9 mmoles), prepared as described in J. Med. Chem., 28(9), 1269–73 (1985), and 1,5-dibromopentane (12.4 g; 53.9 mmoles) in THF (200 ml) and DMF (20 ml).

The reaction mixture was heated under reflux under stirring for 5 hours and then poured into 1N HCl aqueous solution (500 ml).

After extraction with ethyl ether (2×200 ml), the organic phase was washed with water, dried on Na$_2$SO$_4$ and brought to dryness under reduced pressure.

The crude was purified by chromatography (eluent petroleum ether:ethyl acetate=75:25) obtaining 5-bromopentyl-2-[3,4-di(phenylmethoxy)phenyl]ethyl-ether (4 g) as an oil.

$^1$H-NMR (200 MHz; CDCl$_3$): δ(ppm): 1.37–1.65 (m, 4H); 1.76–1.92 (m, 2H); 2.77 (t, 2H); 3.38 (t, 2H); 3.39 (t, 2H); 3.55 (t, 2H); 5.12 (s, 2H); 5.13 (s, 2H); 6.68–6.88 (m, 3H); 7.23–7.49 (m, 10H).

Mass: 483 and 485 [M+1].

Iodine (20 mg) and, after 10 minutes, dropwise a solution of 5-bromopentyl-2-[3,4-di(phenylmethoxy)phenyl]ethyl-ether (3.8 g; 7.9 mmoles) in THF (25 ml) were added to a suspension of magnesium turnings (0.2 g; 8.3 mmoles) in THF (5 ml), under nitrogen at room temperature.

The reaction mixture was heated under reflux for 5 hours, then cooled at room temperature and poured into a flask containing dry ice.

After heating at room temperature, ethyl ether and 1N HCl aqueous solution were added.

The phases were separated and the organic phase was dried on Na$_2$SO$_4$.

After evaporation to dryness under reduced pressure, the crude was purified by chromatography (eluent CH$_2$Cl$_2$:CH$_3$OH:HCOOH 50%=95:5:0.5) obtaining Intermediate 14 (2 g) as a white solid.

$^1$H-NMR (200 MHz; CDCl$_3$): δ(ppm): 1.24–1.71 (m, 6H); 2.32 (t, 2H); 2.77 (t, 2H); 3.35–3.66 (m, 4H); 5.12 (s, 2H); 5.13 (s, 2H); 6.68–6.89 (m, 3H); 7.22–7.49 (m, 10H).

Mass: 449 [M+1].

EXAMPLE 4

Preparation of 1-(4-methoxyphenylmethyl)piperazine (Intermediate 15)

4-Methoxyphenylmethylchloride (3.9 g; 25 mmoles) (Aldrich) was added to a solution of piperazine (21.5 g; 250 mmoles), triethylamine (3 g; 30 mmoles) and potassium iodide (4.1 g; 25 mmoles) in DMF (150 ml).

After 5 hours the reaction mixture was poured into water and extracted 3 times with ethyl ether.

The aqueous phase was concentrated to small volume by evaporating the solvents under reduced pressure and extracted again 3 times with ethyl ether.

The organic phases were collected to the previous ones, dried on Na$_2$SO$_4$ and evaporated to dryness under reduced pressure.

The crude was purified by chromatography (eluent CH$_2$Cl$_2$:CH$_3$OH:ammonia 30%=90:10:1) obtaining Intermediate 15 (4.4 g) as an oil.

$^1$H-NMR (200 MHz; CDCl$_3$): δ(ppm): 1.74 (s, 1H); 2.36 (m, 4H); 2.84 (m, 4H); 3.40 (s, 2H); 3.77 (s, 3H); 6.82 (m, 2H); 7.20 (m, 2H).

Mass: 207 [M+1].

EXAMPLE 5

Preparation of (3-chloro-4-t.butyldimethylsilyloxy)phenylacetic acid t.butyldimethylsilylester (Intermediate 16)

Imidazole (1.8 g; 26.4 mmoles) was added, under nitrogen at room temperature, to a solution of (3-chloro-4-hydroxy)phenylacetic acid (1 g; 5.3 mmoles) (Aldrich) and t.butyldimethylsilylchloride (2 g; 13.3 mmoles) in DMF (6 ml).

The reaction mixture was kept under stirring at room temperature for 5 hours, then poured into a 5% Na$_2$CO$_3$ aqueous solution (25 ml) and extracted with hexane (2×30 ml).

The organic phase was dried on Na$_2$SO$_4$ and the solvent was evaporated under reduced pressure obtaining Intermediate 16 (2.2 g) as an oil.

$^1$H-NMR (200 MHz; CDCl$_3$): δ(ppm): 0.19 (s, 6H); 0.21 (s, 6H); 0.85 (s, 9H); 1.00 (s, 9H); 3.50 (s, 2H); 6.81 (d, 1H); 6.99 (dd, 1H); 7.24 (d, 1H).

Mass: 415 [M+1].

By working in a similar way the following compounds were prepared.

(3-nitro-4-t.butyldimethylsilyloxy)phenylacetic acid t.butyldimethylsilylester (Intermediate 17) starting from (3-nitro-4-hydroxy)phenylacetic acid (Aldrich)

$^1$H-NMR (200 MHz; CDCl$_3$): δ(ppm): 0.22 (s, 6H); 0.23 (s, 6H); 0.85 (s, 9H); 0.99 (s, 9H); 3.59 (s, 2H); 6.91 (d, 1H); 7.32 (dd, 1H); 7.70 (d, 1H).

Mass: 426 [M+1].

(3-methoxy-4-t.butyldimethylsilyloxy)phenylacetic acid t.butyldimethylsilylester (Intermediate 18) starting from (3-methoxy-4-hydroxy)phenylacetic acid (Aldrich)

$^1$H-NMR (200 MHz; CDCl$_3$): δ(ppm): 0.11 (s, 6H); 0.20 (s, 6H); 0.82 (s, 9H); 0.96 (s, 9H); 3.50 (s, 2H); 3.77 (s, 3H); 6.64–6.79 (m, 3H).

Mass: 411 [M+1].

EXAMPLE 6

Preparation of 6-[2-[3,4-di(phenylmethoxy)phenyl]ethylthio]hexanoic acid (Intermediate 19)

A solution of bromine (9.6 g; 60.0 mmoles) in anhydrous DMF (50 ml) was added dropwise to a stirred solution of 2-[3,4-di(phenylmethoxy)phenyl]ethanol (20.0 g; 59.8 mmoles) and triphenylphosphine (17.2 g; 65.6 mmoles) in anhydrous DMF (200 ml), kept under nitrogen at 0° C.

The reaction mixture was heated to room temperature and stirred for 1.5 hours, then poured into water and ice and extracted twice with ethyl ether.

The collected organic phases were dried on $Na_2SO_4$ and the solvent was removed under reduced pressure.

The residue was purified by chromatography (eluent petroleum ether:ethyl acetate=95:5) obtaining 2-[3,4-di(phenylmethoxy)phenyl]-1-bromoethane (16.3 g) as a white solid.

$^1$H-NMR (200 MHz; $CDCl_3$): δ(ppm): 3.04 (t, 2H) 3.47 (t, 2H) 5.13 (s, 2H); 5.14 (s, 2H); 6.70 (dd, 1H); 6.78 (d, 1H); 6.87 (d, 1H); 7.25–7.48 (m, 10H).

Mass: 397, 399 [M+1].

A stirred solution of 2-[3,4-di(phenylmethoxy)phenyl]-1-bromoethane (13.9 g; 35.0 mmoles) and thiourea (3.5 g; 46.0 mmoles) in absolute ethanol (50 ml) was heated under reflux for 16 hours, under nitrogen.

The solvent was removed under reduced pressure and an 1.4N NaOH aqueous solution (50 ml) was added.

The mixture was heated under reflux for 1.5 hours, then poured into water and ice.

Concentrated HCl up to pH 1 was added and the mixture was extracted twice with ethyl ether.

The collected organic phases were washed with water, dried on $Na_2SO_4$ and the solvent was removed under reduced pressure obtaining 2-[3,4-di(phenylmethoxy)phenyl]ethanethiol (12.0 g) as an oil.

$^1$H-NMR (200 MHz; $CDCl_3$): δ(ppm): 1.29 (t, 1H); 2.61–2.86 (m, 4H); 5.12 (s, 3H); 5.14 (s, 2H); 6.69 (dd, 1H); 6.77 (d, 1H); 6.85 (d, 1H); 7.25–7.48 (m, 10H).

Mass: 351 [M+1].

Water (90 ml), Aliquat 336® (trioctylmethylammonium chloride) (0.28 g; 0.7 mmoles) and, dropwise, a solution of NaOH (1.7 g; 42.5 mmoles) in water (20 ml) were added at room temperature to a stirred solution of 2-[3,4-di(phenylmethoxy)phenyl]ethanethiol (12.2 g; 34.8 mmoles) and ethyl 6-bromohexanoate (15.5 g; 69. mmoles) in benzene (140 ml).

The mixture was stirred for 1.5 hours at room temperature.

The organic phase was washed with water, dried on $Na_2SO_4$ and the solvent was removed under reduced pressure.

The residue was dissolved in ethanol (110 ml) and a solution of NaOH (4.1 g; 102.5 mmoles) in water (20 ml) was added dropwise.

The mixture was stirred for 1 hour at room temperature. The solvents were removed under reduced pressure, then ethyl ether (100 ml), water (50 ml) and concentrated HCl up to pH 1 were added.

The aqueous phase was extracted twice with ethyl ether (100 ml).

The organic phases were collected, washed with water and dried on $Na_2SO_4$.

Removal of the solvent under reduced pressure gave Intermediate 19 (15.5 g) as a white solid.

$^1$H-NMR (200 MHz; $CDCl_3$): δ(ppm): 1.35–1.75 (m, 6H); 2.47 (t, 2H); 2.51 (t, 2H); 2.63–2.87 (m, 4H); 5.15 (s, 2H); 5.17 (s, 2H); 6.72 (dd, 1H); 6.82 (d, 1H); 6.89 (d, 1H); 7.25–7.50 (m, 10H).

Mass: 465 [M+1].

EXAMPLE 7

Preparation of 5-(2-aminoethyl)-1,3-benzothiazol-2(3H)-one hydrochloride (Intermediate 20)

Trifluoroacetic anhydride (45.9 g; 218.7 mmoles) was added dropwise at room temperature to a stirred suspension of tyramine (10.0 g; 72.9 mmoles) in ethyl ether (100 ml).

The reaction mixture was stirred for 1 hour, then concentrated under reduced pressure.

The residue was dissolved in methanol (150 ml) and the solvent was removed under reduced pressure.

The resultant 4-(2-trifluoroacetylaminoethyl)phenol (16.7 g; 71.6 mmoles) was dissolved in ethyl ether (350 ml) and slowly added at room temperature to a vigorously stirred solution of sodium nitrate (6.1 g; 71.7 mmoles) and cerium nitrate hexahydrate (0.3 g; 0.7 mmoles) in HCl 6N (120 ml).

The reaction mixture was stirred for 5 hours at room temperature, then $CH_2Cl_2$ (350 ml) was added and the phases were separated.

The organic phase was dried on $Na_2SO_4$ and the solvents removed under reduced pressure.

The resultant 2-(4-hydroxy-3-nitrophenyl)-N-trifluoroacetyl-ethylamine (19.1 g; 68.6 mmoles) was dissolved in pyridine (200 ml).

N,N-dimethylthiocarbamoyl chloride (16.9 g; 137.3 moles) was added at room temperature and the reaction mixture was then heated at 55° C. and kept under stirring for 5 hours.

The solvent was evaporated under reduced pressure; chloroform (200 ml) was added and the solvent removed again.

The residue was dissolved in $CH_2Cl_2$ (200 ml) and the solution washed with HCl 1N (100 ml) and then with water (50 ml).

The organic phase was dried on $Na_2SO_4$ and the solvent removed under reduced pressure.

The residue was purified by chromatography (eluent $CH_2Cl_2$:$CH_3OH$=99:1) obtaining O-[2-nitro-4-(2-trifluoroacetylaminoethyl)phenyl]-N,N-dimethylthiocarbamate (19.8 g) as a yellow solid.

$^1$H-NMR (200 MHz; $CDCl_3$): δ(ppm): 2.99 (t, 2H); 3.38 (s, 3H); 3.45 (s, 3H); 3.59–3.61 (m, 2H); 6.41–6.59 (bs, 1H); 7.21 (d, 1H); 7.48 (dd, 1H); 7.94 (d, 1H).

Mass: 366 [M+1].

Neat O-[2-nitro-4-(2-trifluoroacetylaminoethyl)phenyl]-N,N-dimethylthiocarbamate (19.8 g; 54.2 mmoles) was heated at 205° C. for 0.5 hours.

After cooling at room temperature, $CH_2Cl_2$ (200 ml) was added; filtration of the insoluble and evaporation of the solvent under reduced pressure gave a residue which was purified by chromatography (eluent $CH_2Cl_2$:$CH_3OH$=98:2) obtaining S-[2-nitro-4-(2-trifluoroacetylaminoethyl)phenyl]-N,N-dimethylthiocarbamate (17.5 g) as a pale yellow solid.

$^1$H-NMR (200 MHz; $CDCl_3$): δ(ppm): 2.89 (t, 2H); 2.99 and 3.11 (2bs, 6H); 3.40–3.57 (m, 2H); 7.04 (bt, 1H); 7.35 (dd, 1H); 7.61 (d, 1H); 7.72 (d, 1H).

Mass: 366 [M+1].

A stirred suspension of S-[2-nitro-4-(2-trifluoroacetylaminoethyl)phenyl]-N,N-dimethylthiocarbamate (13.2 g; 36.1 mmoles) in water (85 ml) and acetic acid (3.5 ml) was heated under reflux.

Iron powder (14.0 g) was added portionwise in 30 minutes, then the reaction mixture was vigorously stirred under reflux for 2 hours.

After cooling, methanol (50 ml) was added, the mixture was filtered to remove the insoluble and the solvents were evaporated under reduced pressure.

The residue was purified by chromatography (eluent $CH_2Cl_2$:$CH_3OH$=98:2). The resultant solid was dissolved in methanol and the solution was acidified up to pH 1 by adding a solution of HCl in ethyl ether (15% w/v).

S-[2-amino-4-(2-trifluoroacetylaminoethyl)phenyl]-N,N-dimethylthiocarbamate hydrochloride (7.1 g) was obtained as a pale yellow solid.

¹H-NMR (200 MHz; DMSO-$d_6$): δ(ppm): 2.75 (t, 2H); 2.91 and 3.05 (2bs, 6H); 3.30–3.48 (m, 2H); 4.77 (bs, 3H); 6.71 (dd, 1H); 6.88 (d, 1H); 7.21 (d, 1H); 9.58 (bt, 1H).

Mass: 336 [M+1].

A stirred suspension of S-[2-amino-4-(2-trifluoroacetylaminoethyl)phenyl]-N,N-dimethylthiocarbamate hydrochloride (3.5 g; 9.5 mmoles) in water (118 ml) was heated under reflux for 4 hours.

Filtration of the cooled reaction mixture and washing of the solid with water gave 5-(2-trifluoroacetylaminoethyl)-1,3-benzothiazol-2(3H)-one (2.3 g) as a white solid.

5-(2-trifluoroacetylaminoethyl)-1,3-benzothiazol-2(3H)-one (1.7 g) was dissolved in ethanol (17 ml) and HCl 6N (17 ml).

The reaction mixture was heated under reflux for 5 hours; removal of the solvents under reduced pressure gave Intermediate 20 (1.3 g) as a light grey solid.

¹H-NMR (200 MHz; D₂O): δ(ppm): 2.83 (t, 2H); 3.09 (t, 2H); 6.89–6.97 (m, 2H); 7.29 (d, 1H).

Mass: 195 [M+1].

EXAMPLE 8

Preparation of 6-(2-aminoethyl)-1,3-benzothiazol-2(3H)-one hydrobromide (Intermediate 21)

Trifluoroacetic anhydride (21.8 g; 103.6 mmoles) was added dropwise at room temperature to a stirred suspension of 2-(4-nitrophenyl)ethylamine hydrochloride (10.5 g; 51.8 mmoles) (Aldrich) in CH₂Cl₂ (100 ml).

The reaction mixture was kept under stirring for 1 hour, then concentrated under reduced pressure.

The residue was dissolved in methanol (150 ml) and the solvent was removed under reduced pressure.

The resultant 2-(4-nitrophenyl)-N-trifluoroacetyl-ethylamine (13.3 g) was dissolved in ethanol (250 ml) and concentrated HCl (5.1 ml). Pd on charcoal 10% (50% water) (1.3 g) was added and the reaction mixture was kept under stirring under hydrogen pressure (2.7 atm) at room temperature for 1 hour.

Filtration and evaporation of the solvents under reduced pressure gave 4-(2-trifluoroacetylamino)ethylaniline hydrochloride (13.4 g).

A stirred solution of 4-(2-trifluoroacetylamino)ethylaniline hydrochloride (13.1 g; 48.8 mmoles) and potassium thiocyanate (11.9 g; 122.4 moles) in chlorobenzene (150 ml) was heated at 110° C. for 7 hours; after cooling, the reaction mixture was stirred at room temperature for 16 hours, then the solvent was removed under reduced pressure.

Ethyl ether (100 ml) was added to the residue and the suspension was stirred at room temperature for 30 minutes.

After filtration, the solid was suspended under stirring in water (100 ml) at 50° C. for 10 minutes, then filtered and CH₂Cl₂ (40 ml) was added.

The suspension was kept under stirring at room temperature for 15 minutes giving, after filtration, 4-(2-trifluoroacetylaminoethyl)phenylthiourea (11.5 g) as a light brown solid.

¹H-NMR (200 MHz; DMSO-$d_6$): δ(ppm): 2.76 (t, 2H); 3.32–3.47 (m, 2H); 7.11–7.35 (m, 4H); 7.02–7.75 (bs, 2H); 9.49 (bt, 1H); 9.63 (s, 1H).

Mass: 292 [M+1].

Bromine (12.9 g; 80.7 mmoles) was added dropwise at 10° C. to a stirred suspension of 4-(2-trifluoroacetylaminoethyl)phenylthiourea (11.1 g; 38.1 moles) in chloroform (150 ml).

The reaction mixture was kept under stirring at room temperature for 30 minutes, then heated under reflux for 1 hour.

Cooling of the mixture and filtration gave a yellow solid which was washed with a little acetone and suspended in water (200 ml).

A saturated NaHCO₃ solution was added up to complete basification.

Filtration gave 2-amino-6-[(2-trifluoroacetylamino)ethyl]-1,3-benzothiazole (8.6 g) as a white solid.

¹H-NMR (200 MHz; DMSO-$d_6$): δ(ppm): 2.79 (t, 2H); 3.30–3.45 (m, 2H); 7.02 (dd, 1H); 7.24 (d, 1H); 7.38 (bs; 2H); 7.48 (d, 1H); 9.49 (bs, 1H).

Mass: 290 [M+1].

A solution of sodium nitrite (2.9 g; 42.7 mmoles) in water (4.6 ml) was added dropwise in 2 hours at −5° C. to a stirred solution of 2-amino-6-[(2-trifluoroacetylamino)ethyl]-1,3-benzothiazole (4.1 g; 14.2 mmoles) in 85% phosphoric acid (94 ml).

After stirring for further 40 minutes, the mixture was added over a 40 minutes period to a stirred solution of copper sulphate pentahydrate (28.4 g; 113.7 mmoles) and sodium chloride (35.5 g; 607.5 mmoles) in water (124 ml) at −5° C.

The reaction mixture was stirred at −5° C. for 1 hour, then allowed to warm to room temperature overnight.

The suspension was extracted twice with CH₂Cl₂ (2×100 ml); the organic phase was washed in turn with water, saturated NaHCO₃ and brine, then dried on Na₂SO₄ and the solvent was removed under reduced pressure.

The residue was purified by chromatography (eluent petroleum ether:ethyl acetate=8:2) obtaining 2-chloro-6-[(2-trifluoroacetylamino)ethyl]-1,3-benzothiazole (2.7 g) as a white solid.

¹H-NMR (200 MHz; CDCl₃): δ(ppm): 3.00 (t, 2H); 3.59–3.61 (m, 2H); 6.35–6.63 (bs, 1H); 7.28 (dd, 1H); 7.59 (d, 1H); 7.84 (d, 1H).

Mass: 309 [M+1].

A 5.4M solution of sodium methoxide in methanol (2.7 ml) was added at room temperature to a stirred solution of 2-chloro-6-[(2-trifluoroacetylamino)ethyl]-1,3-benzothiazole (2.1 g; 6.8 mmoles) in methanol (24 ml).

The reaction mixture was heated at 80° C. for 5 hours, then water (3.5 ml) was added and the heating continued for 2 hours.

The solvents were evaporated under reduced pressure, then water and CH₂Cl₂ were added to the residue.

The phases were separated and the organic phase was washed with brine, dried on Na₂SO₄ and the solvent removed under reduced pressure.

The resultant 6-(2-aminoethyl)-2-methoxy-1,3-benzothiazole (1.3 g) was dissolved in 48% HBr (9 ml) and the reaction mixture was stirred under reflux for 1 hour.

Cooling at 0° C. and filtration gave Intermediate 21 (1.3 g) as a light brown solid.

¹H-NMR (200 MHz; D₂O): δ(ppm): 2.82 (t, 2H); 3.10 (t, 2H); 6.94 (d, 1H); 7.05 (dd, 1H); 7.21 (d, 1H).

Mass: 195 [M+1].

EXAMPLE 9

Preparation of 2-amino-6-(2-aminoethyl)-1,3-benzothiazole dihydrochloride (Intermediate 22)

HCl 6N (20 ml) was added at room temperature to a stirred solution of 2-amino-6-[(2-trifluoroacetylamino) ethyl]-1,3-benzothiazole (0.96 g; 3.3 mmoles), prepared as described in example 8, in absolute ethanol (20 ml).

The reaction mixture was heated under reflux for 24 hours, then the solvents were evaporated under reduced pressure obtaining Intermediate 22 (0.84 g) as a white solid.

$^1$H-NMR (200 MHz; DMSO-$d_6$+$D_2$O): δ(ppm): 2.86–3.09 (m, 4H); 7.32 (dd, 1H); 7.45 (d, 1H); 7.75 (d, 1H).

Mass: 194 [M+1].

EXAMPLE 10

Preparation of 2-(3-chloro-5-methoxyphenyl)ethylamine (Intermediate 23)

A solution of 3-chloro-5-methoxybenzyl alcohol (3.4 g; 19.7 mmoles), prepared as described in J. Chem. Soc., Perkin Trans. 1, 4, 1095–8 (1982), and DMF (76 µl) in $CH_2Cl_2$ (20 ml) was added dropwise, under nitrogen at room temperature, to a stirred solution of thionyl chloride (2.5 g; 21.0 mmoles) in $CH_2Cl_2$ (30 ml).

The reaction mixture was heated under reflux for 4 hours, then formic acid (50 µl) was added and the mixture stirred for further 30 minutes.

Water (30 ml) was added and the phases were separated; the organic phase was washed with 10% $KHCO_3$, then with water and dried on $Na_2SO_4$.

Evaporation of the solvent under reduced pressure gave 3-chloro-5-methoxybenzyl chloride (3.5 g; 18.3 mmoles) which was dissolved under nitrogen in anhydrous DMSO (35 ml).

Sodium cyanide (1.5 g; 30.6 mmoles) was added and the reaction mixture was stirred at room temperature for 1 hour, then poured into water and ice and extracted with ethyl acetate.

The organic phase was washed with water, dried on $Na_2SO_4$ and the solvent removed under reduced pressure.

The resultant 3-chloro-5-methoxyphenylacetonitrile (3.2 g; 17.6 mmoles) was dissolved under nitrogen in anhydrous THF (100 ml).

Borane-dimethylsulphide complex (2.6 g; 33.7 mmoles) was slowly added at room temperature under stirring.

The reaction mixture was heated under reflux for 3 hours. After cooling to 5° C. a solution of concentrated HCl (2 ml) in methanol (20 ml) was slowly added.

The reaction mixture was heated under reflux for 2 hours, then the solvents were evaporated under reduced pressure.

Water and ethyl acetate were added to the residue and the phases were separated.

The aqueous phase was basified with $NH_4OH$ 30% and extracted with ethyl acetate.

The organic phase was washed with water, dried on $Na_2SO_4$ and the solvent removed under reduced pressure obtaining Intermediate 23 (2.6 g) as an oil.

$^1$H-NMR (200 MHz; $CDCl_3$): δ(ppm): 1.51 (bs; 2H); 2.68 (t, 2H); 2.94 (t, 2H); 3.77 (s, 3H); 6.60–6.79 (m, 3H).

Mass: 186 [M+1].

EXAMPLE 11

Preparation of (S)-N-propyl-N-[(6-amino-1-oxo)hexyl]-5,6-dimethoxy-1,2,3,4-tetrahydro-2-naphthylamine (Intermediate 24)

Triethylamine (12.7 g; 126.1 mmoles) and then a solution of 6-phtalimidohexanoic acid chloride (15.5 g; 55.5 mmoles) in $CH_2Cl_2$ (120 ml) were added to a suspension of (S)-N-propyl-5,6-dimethoxy-1,2,3,4-tetrahydro-2-naphthylamine hydrochloride (14.4 g; 50.4 mmoles) in $CH_2Cl_2$ (150 ml), kept under stirring at room temperature.

The reaction mixture was kept under stirring at room temperature for 1.5 hours.

After addition of water (250 ml) and separation of the phases, the organic phase was washed with water (150 ml), dried on $Na_2SO_4$ and the solvent evaporated under reduced pressure.

The residue was purified by chromatography (eluent petroleum ether:ethyl acetate=6:4) obtaining (S)-N-propyl-N-[(6-phtalimido-1-oxo)hexyl]-5,6-dimethoxy-1,2,3,4-tetrahydro-2-naphthylamine (24.1 g).

$^1$H-NMR (200 MHz; $CDCl_3$): δ(ppm): 0.80–0.94 (2t, 3H); 1.30–2.02 (m, 10H); 2.26–2.38 (m, 2H); 2.59–3.22 (m, 6H); 3.60–3.72 (m, 2H); 3.75–3.84 (4s, 6H); 3.85–4.66 (m, 1H); 6.66–6.82 (m, 2H); 7.64–7.85 (m, 4H).

Mass: 493 [M+1].

A solution of (S)-N-propyl-N-[(6-phtalimido-1-oxo)hexyl]-5,6-dimethoxy-1,2,3,4-tetrahydro-2-naphthylamine (24.1 g; 48.9 mmoles) in 33% ethanolic methylamine (240 ml) was kept under stirring at room temperature for 20 hours.

The reaction mixture was brought to dryness under reduced pressure and the residue was purified by chromatography (eluent $CH_2Cl_2$:$CH_3OH$: ammonia 30%=90:10:1) obtaining Intermediate 24 (11.9 g) as an oil.

$^1$H-NMR (200 MHz; $CDCl_3$): δ(ppm): 0.80–0.93 (2t, 3H); 1.20–2.04 (m, 10H); 2.25–2.48 (m, 2H); 2.58–3.21 (m, 8H); 3.72–3.81 (4s, 6H); 3.82–4.64 (m, 1H) 6.66–6.80 (m, 2H).

Mass: 363 [M+1].

EXAMPLE 12

Preparation of (S)-N-propyl-N-[(6-amino)hexyl]-5,6-dimethoxy-1,2,3,4-tetrahydro-2-naphthylamine dihydrochloride (Intermediate 25)

Borane-dimethylsulphide complex (3 g; 37 mmoles) was slowly added at room temperature, under stirring and under nitrogen, to a solution of Intermediate 24 (2.3 g; 6.34 mmoles), prepared as described in example 11, in THF (40 ml).

At the end of the addition the reaction mixture was heated under reflux for 2 hours.

After cooling at 5° C. a 37% HCl solution (1.5 ml) in methanol (12 ml) was added.

The reaction mixture was heated under reflux again for 1 hour, then concentrated by distilling the solvents at atmospheric pressure and bringing to dryness under reduced pressure.

The residue was dissolved in methanol (30 ml) and the solvent distilled under reduced pressure; methanol (30 ml) was added again and the solvent was evaporated to dryness.

The crude was purified by chromatography (eluent $CH_2Cl_2$:$CH_3OH$:HCOOH 50%=85:15:1).

The resultant solid was dissolved in absolute ethanol and a solution of HCl in ethyl ether (15% w/v) was added up to clearly acid pH.

By evaporation of the solvents under reduced pressure Intermediate 25 (1.9 g) was obtained as an amorphous white solid.

$^1$H-NMR (200 MHz; $D_2O$): δ(ppm): 0.80 (t, 3H); 1.19–1.32 (m, 4H); 1.40–2.20 (m, 8H); 2.44–3.17 (m, 10H); 3.46–3.63 (m, 1H); 3.59 (s, 3H); 3.68 (s, 3H); 6.76–6.85 (2d, 2H).

Mass: 349 [M+1].

EXAMPLE 13

Preparation of (S)-N-Propyl-N-[(6-amino)hexyl]-5,6-dihydroxy-1,2,3,4-tetrahydro-2-naphthylamine dihydrobromide (Intermediate 26)

A solution of Intermediate 25 (1.2 g; 2.87 mmoles), prepared as described in example 12, in 48% HBr (10 ml) was heated under reflux under nitrogen for 5 hours.

The reaction mixture was then brought to dryness under reduced pressure and absolute ethanol (20 ml) was added to the resultant residue.

After evaporation of the solvent, ethyl acetate (20 ml) was added and the solvent was evaporated again.

The resultant crude was purified by crystallization from a mixture absolute ethanol/ethyl acetate obtaining Intermediate 26 (1.2 g) as a white solid.

$^1$H-NMR (200 MHz; D$_2$O): δ(ppm): 0.80 (t, 3H); 1.21–2.19 (m, 12H); 2.39–3.11 (m, 10H); 3.44–3.60 (m, 1H); 6.50 (d, 1H); 6.62 (d, 1H).

Mass: 321 [M+1].

EXAMPLE 14

Preparation of (S)-N-propyl-5,6-di(phenylmethoxy)-1,2,3,4-tetrahydro-2-naphthylamine hydrochloride (Intermediate 27)

A solution of di-t.butyldicarbonate (14.5 g; 66.2 mmoles) in DMF (28 ml) was added under stirring, at room temperature and under nitrogen, to a solution of (S)-N-propyl-5,6-dihydroxy-1,2,3,4-tetrahydro-2-naphthylamine hydrobromide (20 g; 66 mmoles) and triethylamine (6.7 g; 66 mmoles) in DMF (160 ml).

The reaction mixture was kept under stirring for 3 hours, then poured into a mixture of water, ice and ethyl ether.

After addition of HCl 1N up to clearly acid pH, the phases were separated.

The organic phase was washed twice with water, dried on Na$_2$SO$_4$ and evaporated to dryness under reduced pressure.

The residue was dissolved in DMF (250 ml) and potassium carbonate (34.4 g; 248.9 mmoles) and benzyl bromide (26.6 g; 155.5 mmoles) were added to the resultant solution, under stirring at room temperature.

The reaction mixture was heated at 60° C. for 7 hours, then kept under stirring at room temperature for 16 hours and finally poured into a mixture of water and ethyl ether.

After separation of the phases, the organic phase was washed with water, dried on Na$_2$SO$_4$ and the solvent evaporated under reduced pressure.

The residue was purified by chromatography (eluent petroleum ether:ethyl acetate=93:7) obtaining (S)-N-t.butoxycarbonyl-N-propyl-5,6-di(phenylmethoxy)-1,2,3,4-tetrahydro-2-naphthylamine (23 g) as an oil.

$^1$H-NMR (200 MHz; CDCl$_3$): δ(ppm): 0.86 (t, 3H); 1.46 (s, 9H); 1.49–1.98 (m, 4H); 2.52–3.16 (m, 6H); 3.80–4.32 (bs, 1H); 4.99 (s, 2H); 5.10 (s, 2H); 6.74 (d, 1H); 6.81 (d, 1H); 7.25–7.47 (m, 10H).

Mass: 502 [M+1].

A solution of HCl in ethyl acetate (13% w/v) (250 ml) was added to a solution of (S)-N-t.butoxycarbonyl-N-propyl-5,6-di(phenylmethoxy)-1,2,3,4-tetrahydro-2-naphthylamine (23 g; 45.8 mmoles) in ethyl acetate (100 ml), under stirring at room temperature.

After 30 minutes the precipitate was filtered off, washed with ethyl acetate and dried under vacuum at 50° C. for 10 hours, obtaining Intermediate 27 (16.4 g) as a white solid.

$^1$H-NMR (200 MHz; CDCl$_3$): δ(ppm): 0.87 (t, 3H); 1.71–2.54 (m, 4H); 2.28–3.23 (m, 7H); 4.85 (s, 2H); 4.95 (s, 2H); 6.60 (d, 1H); 6.68 (d, 1H); 7.12–7.33 (m, 10H).

Mass: 402 [M+1].

EXAMPLE 15

Preparation of (S)-N-propyl-N-[(6-amino-1-oxo)hexyl]-5,6-di(phenylmethoxy)-1,2,3,4-tetrahydro-2-naphthylamine (Intermediate 28)

A solution of 6-phthalimidohexanoic acid chloride (11.2 g; 40.2 mmoles) in CH$_2$Cl$_2$ (60 ml) was added to a solution of Intermediate 27 (16 g; 36.5 mmoles), prepared as described in example 14, and triethylamine (9.2 g; 91.3 mmoles) in CH$_2$Cl$_2$ (130 ml), kept under stirring at room temperature.

The reaction mixture was kept under stirring at room temperature for 1 hour.

After addition of water and separation of the phases, the organic phase was washed with water (100 ml), dried on Na$_2$SO$_4$ and the solvent was evaporated under reduced pressure.

The residue was dissolve in a 33% ethanolic solution of methylamine (240 ml) and the reaction mixture was kept under stirring at room temperature for 6 hours.

After evaporation of the solvent under reduced pressure, the residue was purified by chromatography (eluent CH$_2$Cl$_2$:CH$_3$OH:ammonia 30%=90:10:1) obtaining Intermediate 28 (10.9 g).

$^1$H-NMR (200 MHz; CDCl$_3$): δ(ppm): 0.81–0.95 (2t, 3H); 1.23–2.02 (m, 10H) 2.26–3.38 (m, 2H); 2.51–3.21 (m, 8H); 3.80–4.61 (m, 1H); 4.99 (2s, 2H); 5.09 (2s, 2H); 6.69–6.87 (m, 2H); 7.25–7.47 (m, 10H).

Mass: 515 [M+1].

EXAMPLE 16

Preparation of (S)-N-propyl-N-(5,6-dimethoxy-1,2,3,4-tetrahydro-2-naphthyl)-5-carboxy-pentanamide (Intermediate 29)

A solution of hexandioic acid chloride monomethylester (5.9 g; 33.3 mmoles) in CH$_2$Cl$_2$ (10 ml) was added to a solution of (S)-N-propyl-5,6-dimethoxy-1,2,3,4-tetrahydro-2-naphthylamine hydrobromide (10 g; 30.3 mmoles) and triethylamine (7.6 g; 75.3 mmoles) in CH$_2$Cl$_2$ (80 ml), under stirring at room temperature.

After 2 hours water (100 ml) was added and the phases were separated.

The organic phase was washed with a 0.2N HCl aqueous solution, then with water, dried on Na$_2$SO$_4$ and evaporated to dryness under reduced pressure.

The residue was dissolved in methanol (50 ml) and a solution of NaOH (3.3 g; 82.5 mmoles) in water (17 ml) was added dropwise, under stirring at room temperature, to the resultant solution.

The reaction mixture was kept under stirring for 3 hours.

After evaporation of the solvents under reduced pressure, the residue was dissolved in water (40 ml).

The solution was washed with ethyl ether (40 ml), then acidified with 37% HCl up to pH 1 and extracted with CH$_2$Cl$_2$ (100 ml).

After drying the organic phase on Na$_2$SO$_4$ and evaporation of the solvent, Intermediate 29 (11.4 g) was obtained as an oil.

$^1$H-NMR (200 MHz; CDCl$_3$): δ(ppm): 0.87 and 0.91 (2t, 3H); 1.48–2.07 (m, 8H); 2.29–2.46 (m, 4H); 2.60–3.27 (m, 6H); 3.77 and 3.80 and 3.82 and 3.83 (4s, 6H); 3.84–4.05 and 4.48–4.67 (2m, 1H); 6.69 (d, 1H); 6.79 (d, 1H).

Mass: 378 [M+1].

By working in a similar way the following compounds were obtained.

(S)-N-propyl-N-[5,6-di(phenylmethoxy)-1,2,3,4-tetrahydro-2-naphthyl]-5-carboxy-pentanamide (Intermediate 30) starting from Intermediate 27, prepared as described in example 14.

$^1$H-NMR (200 MHz; CDCl$_3$): δ(ppm): 0.87 and 0.91 (2t, 3H); 1.47–2.06 (m, 8H); 2.28–2.46 (m, 4H); 2.51–3.27 (m, 6H); 3.82–4.01 and 4.46–4.65 (2m, 1H); 4.98 and 5.01 (2s, 2H); 5.09 and 5.11 (2s, 2H); 6.69–6.88 (m, 2H); 7.25–7.48 (m, 10H).

Mass: 530 [M+1].

(S)-N-propyl-N-[5-methoxy-1,2,3,4-tetrahydro-2-naphthyl]-5-carboxypentanamide (Intermediate 31) starting from (S)-N-propyl-5-methoxy-1,2,3,4-tetrahydro-2-naphthylamine, prepared as described in J. Med. Chem., 29, 912 (1986).

$^1$H-NMR (200 MHz; CDCl$_3$): δ(ppm): 0.88 and 0.91 (2t, 3H); 1.49–2.10 (m, 8H); 2.28–2.46 (m, 4H); 2.48–3.31 (m, 6H); 3.78 and 3.80 (2s, 3H); 3.87–4.07 and 4.49–4.69 (2m, 1H); 6.60–7.17 (m, 3H).

Mass: 348 [M+1].

EXAMPLE 17

Preparation of 4-nitrophenyl (S)-N-propyl-N-[5,6-di(phenylmethoxy)-1,2,3,4-tetrahydro-2-naphthyl]-6-amino-6-oxohexanoate (Intermediate 32)

DMF (25 μl) and thionyl chloride (1.2 g; 10.1 mmoles) were added under nitrogen at room temperature to a stirred solution of Intermediate 30 (3.4 g; 6.4 mmoles), prepared as described in example 16, in CH$_2$Cl$_2$ (18 ml).

After 30 minutes at room temperature, the reaction mixture was evaporated to dryness under reduced pressure.

The resultant residue was dissolved in CH$_2$Cl$_2$ (10 ml) and the solution was added dropwise under nitrogen to a stirred solution of 4-nitrophenol (0.82 g; 5.9 mmoles) and triethylamine (1.2 g; 11.9 mmoles) in CH$_2$Cl$_2$ (16 ml) and DMF (1 ml).

The mixture was stirred at room temperature for 2.5 hours, then water (30 ml) and CH$_2$Cl$_2$ (50 ml) were added.

The organic phase was washed with water, dried on Na$_2$SO$_4$ and the solvent was removed under reduced pressure.

The residue was purified by chromatography (eluent CH$_2$Cl$_2$:CH$_3$OH=99:1) obtaining Intermediate 32 (3.5 g) as an oil.

$^1$H-NMR (200 MHz; CDCl$_3$): δ(ppm): 0.88 and 0.91 (2t, 3H); 1.45–2.02 (m, 8H); 2.26–2.49 (m, 2H); 2.50–3.32 (m, 8H); 3.81–4.00 and 4.44–4.65 (2m, 1H); 4.99 and 5.01 (2s, 2H); 5.09 and 5.11 (2s, 2H); 6.68–6.88 (m, 2H); 7.19–7.48 (m, 12H); 8.18–8.30 (m, 2H).

Mass: 651 [M+1].

EXAMPLE 18

Preparation of (S)-N-propyl-N-[6-[2-(4-methoxyphenylthio)ethylamino]hexyl]-5,6-dimethoxy-1,2,3,4-tetrahydro-2-naphthylamine dihydrochloride (Intermediate 33)

Thionyl chloride (1.4 g; 11.7 mmoles) was added, under stirring at room temperature, to a suspension of Intermediate 1 (2.4 g; 7.7 mmoles), prepared as described in example 1, in CH$_2$Cl$_2$ (20 ml).

After 1 hour the solvent was evaporated under reduced pressure obtaining an oil which was dissolved in CH$_2$Cl$_2$ (10 ml).

The solution was added dropwise to a suspension obtained by adding triethylamine (2.1 g; 21 mmoles), under stirring at room temperature, to a suspension of (S)-N-propyl-5,6-dimethoxy-1,2,3,4-tetrahydro-2-naphthylamine hydrobromide (2.3 g; 7 mmoles) in CH$_2$Cl$_2$ (30 ml).

The reaction mixture was kept under stirring at room temperature for 1 hour.

After addition of water (40 ml) and separation of the phases, the organic phase was washed with acid water, dried on Na$_2$SO$_4$ and brought to dryness under reduced pressure.

The residue was dissolved under nitrogen in THF (20 ml).

Borane-dimethylsulphide complex (3.2 g; 40.8 mmoles) was slowly added to the resultant solution, under stirring at room temperature. At the end of the addition the reaction mixture was heated under reflux for 1.5 hours.

After cooling at 5° C., a solution of 37% HCl (1.3 ml) in methanol (11 ml) was added.

The reaction mixture was heated again under reflux for 1 hour, then concentrated by distilling the solvents at atmospheric pressure and brought to dryness under reduced pressure.

The residue was dissolved in methanol (20 ml) and the solvent distilled under reduced pressure.

After further addition of methanol (20 ml) and evaporation of the solvent to dryness, the resultant crude was purified by chromatography (eluent CH$_2$Cl$_2$:CH$_3$OH:HCOOH 50%=90:10:1).

The resultant product was dissolved in absolute ethanol (20 ml).

After addition of a solution of HCl in ethyl ether (15% w/v) up to clearly acid pH and evaporation of the solvents under reduced pressure, Intermediate 33 (2.1 g) was obtained as an amorphous white solid.

$^1$H-NMR (200 MHz; D$_2$O): δ(ppm): 0.80 (t, 3H); 1.08–2.21 (m, 12H); 2.42–3.21 (m, 14H); 3.41–3.60 (m, 1H); 3.58 (s, 3H); 3.63 (s, 3H); 3.68 (s, 3H); 6.76–7.34 (m, 6H).

Mass: 515 [M+1].

By working in a similar way the following compounds were prepared.

(S)-N-propyl-N-[6-[3-(4-methoxyphenyl)propylamino]hexyl]-5,6-dimethoxy-1,2,3,4-tetrahydro-2-naphthylamine dihydrochloride (Intermediate 34) starting from Intermediate 3.

$^1$H-NMR (200 MHz; D$_2$O): δ(ppm): 0.81 (t, 3H); 1.12–2.22 (m, 14H); 2.44–3.56 (m, 15H); 3.59 (s, 3H); 3.65 (s, 3H); 3.69 (s, 3H); 6.76–7.12 (m, 6H).

Mass (thermospray): 497 [M+1].

(S)-N-propyl-N-[6-(6,7-dimethoxy-1,2,3,4-tetrahydroisoquinolin-2-yl)hexyl]-5,6-dimethoxy-1,2,3,4-tetrahydro-2-naphthylamine dihydrochloride (Intermediate 35) starting from Intermediate 11.

$^1$H-NMR (200 MHz; CDCl$_3$): δ(ppm): 0.98 (t, 3H); 1.33–2.57 (m, 12H); 2.58–3.71 (m, 15H); 3.76 (s, 3H); 3.81 (s, 3H); 3.82 (s, 3H); 3.83 (s, 3H); 4.11–4.43 (m, 2H); 6.58 (s, 1H); 6.70 (s, 1H); 6.74 (d, 1H); 6.82 (d, 1H).

Mass: 525 [M+1].

(S)-N-propyl-N-[6-(2,3-dihydro-indol-1-yl)hexyl]-5,6-dimethoxy-1,2,3,4-tetrahydro-2-naphthylamine dihydrochloride (Intermediate 36) starting from Intermediate 13.

$^1$H-NMR (200 MHz; CDCl$_3$): δ(ppm): 0.93 (t, 3H); 1.15–2.31 (m, 12H); 2.41–3.94 (m, 15H); 3.82 (s, 3H); 3.86 (s, 3H); 6.43–7.16 (m, 6H).

Mass: 451 [M+1].

EXAMPLE 19

Preparation of (S)-N-propyl-N-[6-[2-(4-nitrophenyl)ethylamino]hexyl]-5,6-di(phenylmethoxy)-1,2,3,4-tetrahydro-2-naphthylamine dihydrochloride (Intermediate 37)

By working in a way similar to that described in example 18 but by using Intermediate 27, prepared as described in example 14, and Intermediate 10, prepared as described in example 1, instead of (S)-N-propyl-5,6-dimethoxy-1,2,3,4-tetrahydro-2-naphthylamine hydrobromide and of Intermediate 1 respectively, Intermediate 37 was obtained.

¹H-NMR (200 MHz; DMSO-d₆): δ(ppm): 0.91 (t, 3H); 1.20–2.41 (m, 12H); 2.53–3.25 (m, 14H); 3.40–3.51 (m, 1H); 4.93 (s, 2H); 5.14 (s, 2H); 6.85 (d, 1H); 7.01 (d, 1H); 7.27–7.50 (m, 10H); 7.51–7.61 (m, 2H); 8.16–8.25 (m, 2H).

Mass: 650 [M+1].

EXAMPLE 20

Preparation of (S)-N-propyl-N-[6-[2-(4-phenylmethoxyphenoxy)ethylamino]hexyl]-5,6-dihydroxy-1,2,3,4-tetrahydro-2-naphthylamine dihydrochloride (Intermediate 38)

Thionyl chloride (3 g; 25.2 mmoles) was added, under nitrogen at room temperature, to a suspension of Intermediate 2 (6.4 g; 17.2 mmoles), prepared as described in example 1, in CH₂Cl₂ (52 ml).

After 1 hour the solvent was evaporated under reduced pressure obtaining an oil which was dissolved in CH₂Cl₂ (17 ml).

Sodium tetraborate (5.3 g; 26.3 mmoles) was added under nitrogen to a solution of (S)-N-propyl-5,6-dihydroxy-1,2,3,4-tetrahydro-2-naphthylamine hydrobromide (4 g; 13.2 mmoles) in water (80 ml).

After heating at 70° C. up to complete dissolution and cooling at room temperature, CH₂Cl₂ (10 ml), potassium carbonate (14.2 g; 102.7 mmoles) and, under vigorous stirring, the above prepared solution in CH₂Cl₂ were added.

After 1 hour at room temperature, the reaction mixture was acidified with HCl 37% up to pH 1 and the phases were separated.

The aqueous phase was extracted with CH₂Cl₂ (50 ml). The collected organic phases were washed with brine slightly acid by HCl, dried on Na₂SO₄ and brought to dryness under reduced pressure.

The resultant residue was dissolved, under nitrogen at room temperature, in THF (40 ml).

Borane-dimethylsulphide complex (6.2 g; 78.9 mmoles) was slowly added to the resultant solution, under stirring at room temperature. At the end of the addition the reaction mixture was heated under reflux for 1.5 hours.

After cooling at 5° C., a solution of HCl 37% (3 ml) in methanol (27 ml) was added.

The reaction mixture was heated again under reflux for 1 hour, then concentrated by distilling the solvents at atmospheric pressure and brought to dryness under reduced pressure.

The residue was distilled in methanol (50 ml) and the solvent distilled under reduced pressure.

After further addition of methanol (50 ml) and evaporation of the solvent up to dryness, the resultant residue was dissolved in absolute ethanol (50 ml). After addition of a solution of HCl in ethyl ether (15% w/v) (2 ml) and evaporation of the solvents under reduced pressure, the crude was purified by chromatography (eluent CH₂Cl₂:CH₃OH:HCOOH 50%=90:10:1).

The resultant solid was dissolved in absolute ethanol (50 ml); after addition of a solution of HCl in ethyl ether (15% w/v) up to a clearly acid pH and evaporation of the solvents under reduced pressure, Intermediate 38 (4 g) was obtained as an amorphous white solid.

¹H-NMR (200 MHz; D₂O): δ(ppm): 0.81 (t, 3H); 1.15–2.20 (m, 12H); 2.34–3.15 (m, 10H); 3.25–3.32 (m, 2H); 3.39–3.59 (m, 1H); 4.05–4.13 (m, 2H); 4.91 (s, 2H); 6.49 (d, 1H); 6.63 (d, 1H); 6.71–6.89 (m, 4H); 7.21–7.33 (m, 5H).

Mass: 547 [M+1].

By working in a similar way the following compounds were prepared.

(S)-N-propyl-N-[6-[2-[3,4-di(phenylmethoxy)phenyl]ethoxy]hexyl]-5,6-dihydroxy-1,2,3,4-tetrahydro-2-naphthylamine hydrochloride (Intermediate 39) starting from Intermediate 14.

Mass: 638 [M+1].

(S)-N-propyl-N-[6-[3-(2-methoxyphenyl)propylamino]hexyl]-5,6-dihydroxy-1,2,3,4-tetrahydro-2-naphthylamine dihydrochloride (Intermediate 40) starting from Intermediate 6.

¹H-NMR (300 MHz; D₂O): δ(ppm): 0.78 (t, 3H); 1.16–2.17 (m, 14H); 2.52 (t, 2H); 2.37–3.18 (m, 12H); 3.43–3.58 (m, 1H); 3.66 (s, 3H); 6.48 (d, 1H); 6.61 (d, 1H); 6.76–7.16 (m, 4H).

Mass: 469 [M+1].

(S)-N-propyl-N-[6-[2-[3,4-di-(phenylmethoxy)phenyl]ethylthio]hexyl]-5,6-dihydroxy-1,2,3,4-tetrahydro-2-naphthylamine hydrochloride (Intermediate 41) starting from Intermediate 19.

¹H-NMR (200 MHz; CDCl₃+D₂O): δ(ppm): 0.95 (t, 3H); 1.15–2.56 (m, 16H); 2.57–3.47 (m, 11H); 5.07 (s, 2H); 5.09 (s, 2H); 6.65–6.88 (m, 5H); 7.21–7.45 (m, 10H).

Mass: 654 [M+1].

EXAMPLE 21

Preparation of (S)-N-propyl-N-[6-[2-(3-chloro-4-hydroxyphenyl)ethylamino]hexyl]-5,6-dimethoxy-1,2,3,4-tetrahydro-2-naphthylamine dihydrochloride (Intermediate 42)

DMF (2 drops) and oxalyl chloride (0.8 g; 6.3 mmoles) were added, under nitrogen at 0° C., to a solution of Intermediate 16 (2.2 g, 5.3 mmoles), prepared as described in example 5, in CH₂Cl₂ (4 ml).

The reaction mixture was kept under stirring at 0° C. for 1.5 hours, then allowed to heat spontaneously to room temperature.

After evaporation of the solvent under reduced pressure, the resultant residue was dissolved in CH₂Cl₂ (5 ml).

The solution was added dropwise, under nitrogen at room temperature, to a solution of Intermediate 24 (1.9 g; 5.3 mmoles), prepared as described in example 11, and triethylamine (1.6 g; 16 mmoles) in CH₂Cl₂ (5 ml).

After 3 hours water (10 ml) was added, the phases were separated and the aqueous phase was extracted with CH₂Cl₂ (10 ml).

The collected organic phases were dried on Na₂SO₄ and the solvent evaporated under reduced pressure.

The residue was dissolved in ethyl ether (20 ml) and tetrabutylammonium fluoride trihydrate (3.4 g; 10.8 mmoles) was added to the solution.

After 2 hours under stirring at room temperature, the solvent was evaporated under reduced pressure and the residue was parted between water and CH₂Cl₂.

The organic phase was dried on Na₂SO₄ and the solvent evaporated under reduced pressure.

The resultant crude was purified by chromatography (eluent CH₂Cl₂:CH₃OH=98:2) obtaining (S)-N-propyl-N-[6-[(3-chloro-4-hydroxyphenyl)acetylamino]-1-oxohexyl]-5,6-dimethoxy-1,2,3,4-tetrahydro-2-naphthylamine (1.7 g) as an oil.

¹H-NMR (200 MHz; CDCl₃): δ(ppm): 0.86 and 0.91 (2t, 3H); 1.17–2.07 (m, 10H); 2.24–2.42 (m, 2H); 2.58–3.30 (m, 8H); 3.42 (s, 2H); 3.76 and 3.80 and 3.81 and 3.82 (4s, 6H); 3.83–4.04 and 4.46–4.66 (2m, 1H); 5.89 (bt, 1H); 6.43 (bs, 1H); 6.70 (d, 1H); 6.80 (d, 1H); 6.88–7.26 (m, 3H).

Mass: 531 [M+1].

By working in a similar way (S)-N-propyl-N-[6-[(3-nitro-4-hydroxyphenyl)acetylamino]-1-oxohexyl]-5,6-dimethoxy-1,2,3,4-tetrahydro-2-naphthylamine was prepared starting from Intermediate 17.

¹H-NMR (200 MHz; CDCl₃): δ(ppm): 0.87 and 0.91 (2t, 3H); 1.21–2.08 (m, 10H); 2.27–2.41 (m, 2H) 2.57–3.35 (m, 8H); 3.48 and 3.49 (2s, 2H); 3.76 and 3.79 and 3.80 and 3.82 (4s, 6H); 3.85–4.05 and 4.43–4.65 (2m, 1H); 6.37 and 6.42 (2bt, 1H); 6.70 (d, 1H); 6.80 (d, 1H); 7.02–8.02 (m, 3H); 10.47 (bs, 1H).

Mass: 542 [M+1].

Borane-dimethylsulphide complex (1.6 g; 20.3 mmoles) was slowly added, under stirring and under nitrogen, to a solution of (S)-N-propyl-N-[6-[(3-chloro-4-hydroxyphenyl)acetylamino]-1-oxohexyl]-5,6-dimethoxy-1,2,3,4-tetrahydro-2-naphthylamine (1.7 g; 3.2 mmoles) in THF (10 ml). At the end of the addition the reaction mixture was heated under reflux for 1.5 hours.

After cooling at 5° C., a solution of HCl 37% (0.8 ml) in methanol (7 ml) was added.

The reaction mixture was heated again under reflux for 1 hour, then concentrated by distilling the solvents at atmospheric pressure and brought to dryness under reduced pressure.

The residue was dissolved in methanol (15 ml) and the solvent distilled under reduced pressure.

After further addition of methanol (15 ml) and evaporation of the solvent up to dryness, the resultant residue was dissolved in absolute ethanol (15 ml). After addition of a solution of HCl in ethyl ether (15% w/v) (0.5 ml) and evaporation of the solvents under reduced pressure, the crude was purified by chromatography (eluent CH₂Cl₂:CH₃OH:HCOOH 50%=85:15:1).

The resultant solid was dissolved in absolute ethanol (20 ml); after addition of a solution of HCl in ethyl ether (15% w/v) up to a clearly acid pH and evaporation of the solvents under reduced pressure, Intermediate 42 (1.4 g) was obtained as an amorphous white solid.

¹H-NMR (200 MHz; D₂O): δ(ppm): 0.82 (t, 3H); 1.17–1.32 (m, 4H); 1.39–2.24 (m, 8H); 2.46–3.18 (m, 14H); 3.46–3.65 (m, 1H); 3.61 (s, 3H); 3.70 (s, 3H); 6.79–7.18 (m, 5H).

Mass: 503 [M+1].

By working in a similar way the following compound was prepared.

(S)-N-propyl-N-[6-[2-(3-nitro-4-hydroxyphenyl)ethylamino]hexyl]-5,6-dimethoxy-1,2,3,4-tetrahydro-2-naphthylamine dihydrochloride (Intermediate 43) starting from (S)-N-propyl-N-[6-[(3-nitro-4-hydroxyphenyl)acetylamino]-1-oxohexyl]-5,6-dimethoxy-1,2,3,4-tetrahydro-2-naphthylamine.

¹H-NMR (200 MHz; D₂O): δ(ppm): 0.82 (t, 3H); 1.17–2.23 (m, 12H); 2.47–3.24 (m, 14H); 3.47–3.66 (m, 1H); 3.60 (s, 3H); 3.69 (s, 3H); 6.81–7.06 (m, 5H).

Mass: 514 [M+1].

EXAMPLE 22

Preparation of (S)-N-propyl-N-[6-[2-(3-methoxy-4-hydroxyphenyl)ethylamino]hexyl]-5,6-di(phenylmethoxy)-1,2,3,4-tetrahydro-2-naphthylamine dihydrochloride (Intermediate 44)

DMF (2 drops) and oxalyl chloride (0.7 g; 5.5 mmoles) were added to a solution of Intermediate 18 (1.8 g; 4.4 mmoles), prepared as described in example 5, in CH₂Cl₂ (3 ml), under nitrogen at 0° C.

The reaction mixture was kept under stirring at 0° C. for 1.5 hours, then allowed to heat spontaneously to room temperature.

After evaporation of the solvent under reduced pressure, the resultant residue was dissolved in CH₂Cl₂ (3 ml).

The solution was added dropwise, under nitrogen at room temperature, to a solution of Intermediate 28 (2.3 g; 4.4 mmoles), prepared as described in example 15, and triethylamine (1.3 g; 13.1 mmoles) in CH₂Cl₂ (3 ml).

After 4 hours water (10 ml) was added, the phases were separated and the aqueous phase was extracted with CH₂Cl₂ (10 ml).

The collected organic phases were dried on Na₂SO₄ and the solvent evaporated under reduced pressure.

The residue was dissolved in ethyl ether (15 ml) and tetrabutylammonium fluoride trihydrate (2.8 g; 8.9 mmoles) was added to the solution.

After 2 hours under stirring at room temperature, the solvent was evaporated under reduced pressure and the residue was parted between water and CH₂Cl₂.

The organic phase was dried on Na₂SO₄ and the solvent evaporated under reduced pressure.

The resultant crude was purified by chromatography (eluent CH₂Cl₂:CH₃OH=98:2) obtaining (S)-N-propyl-N-[6-[(3-methoxy-4-hydroxyphenyl)acetylamino]-1-oxohexyl]-5,6-di(phenylmethoxy)-1,2,3,4-tetrahydro-2-naphthylamine (2.8 g) as an oil.

¹H-NMR (200 MHz; CDCl₃): δ(ppm): 0.86 and 0.91 (2t, 3H); 1.16–2.00 (m, 10H); 2.22–2.36 (m, 2H); 2.51–3.27 (m, 8H); 3.45 and 3.46 (2s, 2H); 3.85 and 3.86 (2s, 3H); 3.75–3.98 and 4.41–4.63 (2m, 1H); 4.98 and 5.01 (2s, 2H); 5.09 and 5.11 (2s, 2H); 5.61 (bt, 1H); 6.67–6.88 (m, 5H); 7.24–7.48 (m, 10H).

Mass: 679 [M+1].

Borane-dimethylsulphide complex (1.9 g; 24.2 mmoles) was slowly added to a solution of (S)-N-propyl-N-[6-[(3-methoxy-4-hydroxyphenyl)acetylamino]-1-oxohexyl]-5,6-di(phenylmethoxy)-1,2,3,4-tetrahydro-2-naphthylamine (2.8 g; 4.1 mmoles) in THF (25 ml), under stirring and under nitrogen. At the end of the addition the reaction mixture was heated under reflux for 1.5 hours.

After cooling at 5° C., a solution of HCl 37% (0.9 ml) in methanol (8 ml) was added.

The reaction mixture was heated again under reflux for 1 hour, then concentrated by distilling the solvents at atmospheric pressure and brought to dryness under reduced pressure.

The residue was dissolved in methanol (20 ml) and the solvent distilled under reduced pressure.

After further addition of methanol (20 ml) and evaporation of the solvent up to dryness, the resultant residue was dissolved in absolute ethanol (20 ml). After addition of a solution of HCl in ethyl ether (15% w/v) (0.5 ml) and evaporation of the solvents under reduced pressure, the crude was purified by chromatography (eluent CH₂Cl₂:CH₃OH:HCOOH 50%=90:10:1).

The resultant solid was dissolved in absolute ethanol (20 ml); after addition of a solution of HCl in ethyl ether (15% w/v) up to clearly acid pH and evaporation of the solvents under reduced pressure, Intermediate 44 (1.5 g) was obtained as an amorphous white solid.

$^1$H-NMR (200 MHz; DMSO-$d_6$): δ(ppm): 0.91 (t, 3H); 1.18–2.39 (m, 12H); 2.51–3.65 (m, 15H); 3.75 (s, 3H) 4.93 (s, 2H); 5.16 (s, 2H); 6.58–7.04 (m, 5H); 7.26–7.50 (m, 10H); 8.88 (bs, 1H); 9.08 (bs, 2H); 10.47 (bs, 1H).

Mass: 651 [M+1].

EXAMPLE 23

Preparation of (S)-N-propyl-N-[6-[3-(3,4-dimethoxyphenyl)propylamino]hexyl]-5,6-dimethoxy-1,2,3,4-tetrahydro-2-naphthylamine dihydrochloride (Intermediate 45)

DMF (2 drops) and thionyl chloride (1.2 g; 10.1 mmoles) were added to a solution of 3-(3,4-dimethoxyphenyl) propionic acid (1.4 g; 6.6 mmoles) (Aldrich) in $CH_2Cl_2$ (10 ml), under nitrogen at room temperature.

After 1 hour the solvent was evaporated under reduced pressure obtaining an oil which was dissolved in $CH_2Cl_2$ (5 ml).

Triethylamine (0.8 g; 7.9 mmoles) and the above prepared solution in $CH_2Cl_2$ were added to a solution of Intermediate 24 (2 g; 5.5 mmoles), prepared as described in example 11, in $CH_2Cl_2$ (15 ml), kept under stirring at room temperature.

The reaction mixture was kept under stirring at room temperature for 3 hours.

After addition of water (30 ml) and separation of the phases, the organic phase was dried on $Na_2SO_4$ and the solvent evaporated under reduced pressure.

The resultant residue was dissolved in THF (15 ml).

Borane-dimethylsulphide complex (2.6 g; 32.5 mmoles) was slowly added, under stirring and under nitrogen at room temperature, to the resultant solution. At the end of the addition the reaction mixture was heated under reflux for 1.5 hours.

After cooling at 5° C., a solution of HCl 37% (1 ml) in methanol (7.5 ml) was added.

The reaction mixture was heated again under reflux for 1 hour, then concentrated by distilling the solvents at atmospheric pressure and brought to dryness under reduced pressure.

The residue was dissolved in methanol (30 ml) and the solvent distilled under reduced pressure.

After further addition of methanol (30 ml) and evaporation of the solvent up to dryness, the resultant residue was dissolved in absolute ethanol (30 ml). After addition of a solution of HCl in ethyl ether (15% w/v) (1 ml) and evaporation of the solvents under reduced pressure, the crude was purified by chromatography (eluent $CH_2Cl_2$:$CH_3OH$:HCOOH 50%=90:10:1).

The resultant solid was dissolved in absolute ethanol; after addition of a solution of HCl in ethyl ether (15% w/v) up to clearly acid pH and evaporation of the solvents under reduced pressure, Intermediate 45 (1.3 g) was obtained as an amorphous white solid.

$^1$H-NMR (200 MHz; $D_2O$): δ(ppm): 0.82 (t, 3H); 1.15–2.21 (m, 14H); 2.50 (t, 2H); 2.47–3.20 (m, 12H); 3.43–3.61 (m, 1H); 3.59 (s, 3H); 3.66 (s, 3H); 3.68 (s, 3H); 3.69 (s, 3H); 6.65–6.86 (m, 5H).

Mass: 527 [M+1].

By working in a similar way the following compounds were prepared.
(S)-N-propyl-N-[6-[2-(3-methyl-4-methoxyphenyl) ethylamino]hexyl]-5,6-dimethoxy-1,2,3,4-tetrahydro-2-naphthylamine dihydrochloride (Intermediate 46) starting from (3-methyl-4-methoxyphenyl)acetic acid, prepared as described in Chem. Pharm. Bull., 30(7), 2440–6 (1982).

$^1$H-NMR (200 MHz; $D_2O$): δ(ppm): 0.83 (t, 3H); 1.13–2.25 (m, 12H); 2.04 (s, 3H); 2.48–3.22 (m, 14H); 3.45–3.65 (m, 1H); 3.62 (s, 3H); 3.69 (s, 3H); 3.71 (s, 3H); 6.80–7.03 (m, 5H).

Mass: 497 [M+1].

(S)-N-propyl-N-[6-[2-(3,5-dimethoxy-4-methylphenyl) ethylamino]hexyl]-5,6-dimethoxy-1,2,3,4-tetrahydro-2-naphthylamine dihydrochloride (Intermediate 47) starting from (3,5-dimethoxy-4-methylphenyl)acetic acid, prepared as described in J. Chem. Res. Synop. (5), 149 (1981)

$^1$H-NMR (200 MHz; $D_2O$): δ(ppm): 0.81 (t, 3H); 1.13–2.20 (m, 12H); 1.82 (s, 3H); 2.42–3.19 (m, 14H); 3.52 (m, 1H); 3.57 (s, 3H); 3.65 (s, 6H); 3.67 (s, 3H); 6.48 (s, 2H); 6.75 (d, 1H); 6.81 (d, 1H).

Mass: 527 [M+1].

(S)-N-propyl-N-[6-[2-(4-methoxy-3-phenylmethoxyphenyl)ethylamino]hexyl]-5,6-di(phenylmethoxy)-1,2,3,4-tetrahydro-2-naphthylamine dihydrochloride (Intermediate 48) starting from Intermediate 28 and (4-methoxy-3-phenylmethoxyphenyl)acetic acid, prepared as described in J. Org. Chem., 49(26), 5243–6 (1984)

$^1$H-NMR (200 MHz; DMSO-$d_6$): δ(ppm): 0.92 (t, 3H); 1.20–2.42 (m, 12H); 2.52–3.65 (m, 15H); 3.72 (s, 3H); 4.93 (s, 2H); 5.06 (s, 2H); 5.15 (s, 2H); 6.74–7.04 (m, 5H); 7.27–7.51 (m, 15H); 9.10–9.35 (bs, 2H); 10.50–10.71 (bs, 1H).

Mass (thermospray): 741 [M+1].

EXAMPLE 24

Preparation of (S)-N-propyl-N-[6-[4-(4-methoxyphenylmethyl)piperazin-1-yl]hexyl]-5,6-dimethoxy-1,2,3,4-tetrahydro-2-naphthylamine trihydrochloride (Intermediate 49)

Thionyl chloride (1.1 g; 9.2 mmoles) was added to a solution of Intermediate 29 (2.3 g; 6.1 mmoles), prepared as described in example 16, in $CH_2Cl_2$ (15 ml), under nitrogen at room temperature.

After 1 hour the solvent was evaporated under reduced pressure obtaining an oil which was dissolved in $CH_2Cl_2$ (5 ml).

The above prepared solution in $CH_2Cl_2$ was added to a solution of Intermediate 15 (1.2 g; 5.8 mmoles), prepared as described in example 4, and triethylamine (0.8 g; 7.9 mmoles) in $CH_2Cl_2$ (15 ml), kept under stirring at room temperature.

The reaction mixture was kept under stirring at room temperature for 2 hours.

After addition of water (30 ml) and separation of the phases, the aqueous phase was extracted with $CH_2Cl_2$ (20 ml).

The collected organic phases were washed with water, dried on $Na_2SO_4$ and the solvent evaporated under reduced.

The resultant residue was dissolved in THF (15 ml).

Borane-dimethylsulphide complex (3.3 g; 42 mmoles) was slowly added to the resultant solution, under stirring and under nitrogen at room temperature. At the end of the addition the reaction mixture was heated under reflux for 1.5 hours.

After cooling at 5° C., a solution of HCl 37% (1.4 ml) in methanol (12 ml) was added.

The reaction mixture was heated again under reflux for 1 hour, then concentrated by distilling the solvents at atmospheric pressure and brought to dryness under reduced pressure.

The residue was dissolved in methanol (30 ml) and the solvent distilled under reduced pressure.

After further addition of methanol (30 ml) and evaporation of the solvent up to dryness, the resultant residue was dissolved in absolute ethanol (30 ml). After addition of a solution of HCl in ethyl ether (15% w/v) (1 ml), the solvents were evaporated obtaining Intermediate 49 (2.5 g) as an amorphous white solid.

$^1$H-NMR (200 MHz; D$_2$O): δ(ppm): 0.82 (t, 3H); 1.8–2.24 (m, 12H); 2.46–3.23 (m, 10H); 3.31–3.65 (m, 9H); 3.61 (s, 3H); 3.70 (s, 6H); 4.24 (s, 2H); 6.84 (s, 2H); 6.90–7.36 (m, 4H).

Mass: 538 [M+1].

By working in a similar way the following compounds were prepared.

(S)-N-propyl-N-[6-[2-(2-oxo-3H-1,3-benzothiazol-6-yl) ethylamino]hexyl]-5,6-dimethoxy-1,2,3,4-tetrahydro-2-naphthylamine dihydrochloride (Intermediate 50) starting from Intermediate 21.

$^1$H-NMR (200 MHz; D$_2$O): δ(ppm): 0.80 (t, 3H); 1.13–2.20 (m, 12H); 2.40–3.20 (m, 14H); 3.42–3.61 (m, 1H); 3.57 (s, 3H); 3.66 (s, 3H); 6.74 (d, 1H); 6.78 (d, 1H); 6.95–7.26 (m, 3H).

Mass: 526 [M+1].

(S)-N-propyl-N-[6-[2-(2-oxo-3H-1,3-benzothiazol-5-yl) ethylamino]hexyl]-5,6-dimethoxy-1,2,3,4-tetrahydro-2-naphthylamine dihydrochloride (Intermediate 51) starting from Intermediate 20.

$^1$H-NMR (200 MHz; DMSO-d$_6$): δ(ppm): 0.93 (t, 3H); 1.15–2.42 (m, 12H); 2.52–3.65 (m, 15H); 3.68 (s, 3H); 3.76 (s, 3H); 6.83 (d, 1H); 6.90 (d, 1H); 7.00–7.08 (m, 2H); 7.52 (d, 1H); 9.02–9.30 (bs, 2H); 10.34–10.54 (bs, 1H); 12.04 (s, 1H).

Mass: 526 [M+1].

(S)-N-propyl-N-[6-[2-(2-amino-1,3-benzothiazol-6-yl) ethyamino]hexyl]-5,6-dimethoxy-1,2,3,4-tetrahydro-2-naphthylamine trihydrochloride (Intermediate 52) starting from Intermediate 22.

$^1$H-NMR (200 MHz; D$_2$O): δ(ppm): 0.80 (t, 3H); 1.14–2.22 (m, 12H); 2.41–3.22 (m, 14H); 3.44–3.64 (m, 1H); 3.57 (s, 3H); 3.67 (s, 3H); 6.80 (s, 2H); 7.23 (dd, 1H); 7.30 (d, 1H); 7.50 (d, 1H).

Mass (thermospray): 525 [M+1].

(S)-N-propyl-N-[6-[2-(3-chloro-5-methoxyphenyl) ethylamino]hexyl]-5,6-dimethoxy-1,2,3,4-tetrahydro-2-naphthylamine dihydrochloride (Intermediate 53) starting from Intermediate 23.

$^1$H-NMR (200 MHz; CDCl$_3$): δ(ppm): 0.86 (t, 3H); 1.18–2.09 (m, 12H); 2.38–3.13 (m, 15H); 3.76 (s, 3H); 3.77 (s, 3H); 3.81 (s, 3H); 6.60–6.82 (m, 5H).

Mass: 517 [M+1].

(S)-N-propyl-N-[6-[2-(2-oxo-3H-1,3-benzothiazol-6-yl) ethylamino]hexyl]-5-methoxy-1,2,3,4-tetrahydro-2-naphthylamine dihydrochloride (Intermediate 54) starting from Intermediate 21 and Intermediate 31.

$^1$H-NMR (200 MHz; DMSO-d$_6$): δ(ppm): 0.93 (t, 3H); 1.19–2.45 (m, 12H); 2.68–3.32 (m, 14H) 3.50–3.68 (m, 1H); 3.76 (s, 3H); 6.67–7.51 (m, 6H); 9.25 (bs, 2H); 10.60 (bs, 1H).

Mass: 496 [M+1].

EXAMPLE 25

Preparation of (S)-N-propyl-N-[6-[(3,4-dimethoxyphenyl) acetylamino]hexyl]-5,6-dimethoxy-1,2,3,4-tetrahydro-2-naphthylamine (Intermediate 55)

DMF (2 drops) and thionyl chloride (0.8 g; 6.7 mmoles) were added to a solution of (3,4-dimethoxyphenyl)acetic acid (0.8 g; 4.1 mmoles) (Aldrich) in CH$_2$Cl$_2$ (7 ml), under nitrogen at room temperature.

After 1 hour the solvent was evaporated under reduced pressure obtaining an oil which was dissolved in CH$_2$Cl$_2$ (5 ml).

The above prepared solution in CH$_2$Cl$_2$ was added to a solution of Intermediate 25 (1.4 g; 3.3 mmoles), prepared as described in example 12, and triethylamine (1.2 g; 11.9 mmoles) in CH$_2$Cl$_2$ (14 ml), kept under stirring at room temperature.

The reaction mixture was kept under stirring at room temperature for 3 hours and then poured into water (25 ml).

After separation of the phases, the aqueous phase was extracted with CH$_2$Cl$_2$ (25 ml) and the collected organic phases were washed with water, dried on Na$_2$SO$_4$ and the solvent evaporated under reduced pressure.

The resultant crude was purified by chromatography (eluent CH$_2$Cl$_2$: CH$_3$OH:ammonia 30%=95:5:0.5) obtaining Intermediate 55 (0.6 g) as an oil.

$^1$H-NMR (200 MHz; CDCl$_3$): δ(ppm): 0.86 (t, 3H); 1.14–2.12 (m, 12H); 2.38–3.23 (m, 10H); 3.49 (s, 2H); 3.76 (s, 3H); 3.81 (s, 3H); 3.85 (s, 6H); 5.44 (bs, 1H); 6.68–6.86 (m, 5H).

Mass: 527 [M+1].

EXAMPLE 26

Preparation of (S)-N-propyl-N-[5,6-di(phenylmethoxy)-1,2,3,4-tetrahydro-2-naphthyl]-N'-[2-(4-methoxycarbonylphenyl)ethyl]-1,6-hexandiamide (Intermediate 56)

Thionyl chloride (1.25 g; 10.5 mmoles) was added under nitrogen to a solution of Intermediate 30 (3.7 g; 7.0 mmoles), prepared as described in example 16, in CH$_2$Cl$_2$.

After 2 hours at room temperature, the reaction mixture was evaporated to dryness under reduced pressure.

The resultant residue was dissolved in CH$_2$Cl$_2$ (5 ml) and the solution was added dropwise under nitrogen to a stirred solution of methyl 4-(2-aminoethyl)benzoate (1.5 g; 7.0 mmoles), prepared as described in Berichte, 71, 59 (1938) and triethylamine (1.8 g; 17.5 mmoles) in CH$_2$Cl$_2$ (40 ml).

After 2 hours at room temperature water (30 ml) was added and the phases were separated.

The aqueous phase was extracted with CH$_2$Cl$_2$ (20 ml); the collected organic phases were washed with water, dried on Na$_2$SO$_4$, filtered and the solvent removed under reduced pressure.

The resultant crude was purified by chromatography (eluent CH$_2$Cl$_2$: CH$_3$OH=95:5) obtaining Intermediate 56 (4.0 g) as an amorphous solid.

$^1$H-NMR (200 MHz; CDCl$_3$): δ(ppm): 0.87 and 0.90 (2t, 3H); 1.44–2.03 (m, 8H); 2.09–2.39 (m, 4H); 2.51–3.23 (m, 8H); 3.44–3.58 (m, 2H); 3.79–3.99 and 4.41–4.60 (2m, 1H); 3.87 (s, 3H); 4.98 and 5.01 (2s, 2H); 5.09 and 5.10 (2s, 2H); 6.15–6.29 (m, 1H); 6.70–6.87 (m, 2H), 7.20–7.47 (m, 12H); 7.95 (dd, 1H).

Mass: 691 [M+1].

EXAMPLE 27

Preparation of (S)-N-propyl-N-[6-[2-(4-methoxycarbonylphenyl)ethylamino]hexyl]-5,6-di (phenylmethoxy)-1,2,3,4-tetrahydro-2-naphthylamine (Intermediate 57)

Borane-dimethylsulphide complex (2.0 g; 25.6 mmoles) was slowly added to a solution of Intermediate 56 (4.4 g; 6.4 mmoles), prepared as described in example 26, in THF (100 ml), under stirring and under nitrogen at room temperature.

At the end of the addition the reaction mixture was heated under reflux for 1.5 hours.

After cooling at 5° C., a solution of concentrated HCl (1.4 ml) in methanol (10 ml) was slowly added.

The mixture was heated again under reflux for 2 hours, then concentrated by distilling the solvents at atmospheric pressure and brought to dryness under reduced pressure.

The residue was dissolved in methanol (30 ml) and the solvent distilled under reduced pressure.

Methanol (30 ml) was added and the solvent evaporated again.

Ethyl acetate (50 ml), water (30 ml) and aqueous $NH_4OH$ 30% up to pH 14 were added.

The aqueous phase was extracted with ethyl acetate (30 ml), then the organic phases were collected, washed with water and dried on $Na_2SO_4$.

Evaporation of the solvents under reduced pressure gave a crude which was purified by chromatography (eluent $CH_2Cl_2:CH_3OH:NH_4OH$ 30%=90:10:0.5) obtaining Intermediate 57 (3.0 g) as an oil.

$^1$H-NMR (200 MHz; $CDCl_3$): $\delta$(ppm): 0.86 (t, 3H); 1.18–2.06 (m, 13H); 2.38–3.16 (m, 15H); 3.89 (s, 3H); 4.98 (s, 2H); 5.09 (s, 2H); 6.76 (d, 1H); 6.81 (d, 1H); 7.23–7.48 (m, 12H); 7.91–7.99 (m, 2H).

Mass: 663 [M+1].

EXAMPLE 28

Preparation of (S)-N-propyl-N-[5,6-di(phenylmethoxy)-1,2,3,4-tetrahydro-2-naphthyl]-N'-[2-(4-carboxyphenyl)ethyl]-1,6-hexandiamide (Intermediate 58)

An aqueous solution of NaOH 4N (2 ml) was added dropwise at room temperature to a stirred solution of Intermediate 56 (2.0 g; 2.9 mmoles), prepared as described in example 26, in methanol (10 ml).

The reaction mixture was heated under reflux and under stirring for 2 hours.

The solvents were removed under reduced pressure, then $CH_2Cl_2$ (20 ml), water (20 ml) and concentrated HCl up to pH 1 were added.

The aqueous phase was extracted with $CH_2Cl_2$ (20 ml), then the organic phases were collected, washed with water and dried on $Na_2SO_4$.

Removal of the solvent under reduced pressure gave Intermediate 58 (1.9 g) as a white amorphous solid.

$^1$H-NMR (200 MHz; $CDCl_3$): $\delta$(ppm): 0.87 and 0.90 (2t, 3H); 1.45–2.06 (m, 8H); 2.10–2.47 (m, 4H); 2.50–3.32 (m, 8H); 3.43–3.59 (m, 2H); 3.80–4.00 and 4.41–4.61 (2m, 1H); 4.98 and 5.00 (2s, 2H); 5.09 and 5.10 (2s, 2H); 6.27–6.45 (m, 1H); 6.68–6.87 (m, 2H); 7.21–7.47 (m, 12H); 7.94 (d, 1H).

Mass: 677 [M+1].

EXAMPLE 29

Preparation of (S)-N-propyl-N-[6-[2-(4-sulphophenyl)ethylamino]hexyl]-5,6-di(phenylmethoxy)-1,2,3,4-tetrahydro-2-naphthylamine dihydrochloride (Intermediate 59)

A solution of 4-(2-aminoethyl)benzenesulphonic acid (1.7 g; 8.5 mmoles) (Aldrich) in water (51 ml) was added dropwise at room temperature to a stirred solution of Intermediate 32 (3.5 g; 5.4 mmoles), prepared as described in example 17, in pyridine (210 ml).

The reaction mixture was heated to 70° C. and kept under stirring for 2 hours.

The solvents were removed under reduced pressure, methanol (30 ml) was added and then removed under reduced pressure.

The residue was purified by chromatography (eluent $CH_2Cl_2:CH_3OH:HCOOH$ 50%=85:15:1).

The purified product was dissolved under nitrogen in anhydrous THF (30 ml), then borane-dimethylsulphide complex (1.5 g; 19.0 mmoles) was slowly added at room temperature under stirring.

The reaction mixture was heated under reflux for 2 hours.

After cooling to 5° C., a solution of concentrated HCl (0.7 ml) in methanol (7 ml) was slowly added.

The mixture was heated under reflux for 2 hours, concentrated by distilling the solvents at atmospheric pressure and then under reduced pressure up to dryness.

The residue was dissolved in methanol (20 ml); the solvent was distilled off under reduced pressure, methanol (20 ml) was added and the solvent was removed again.

Absolute ethanol (20 ml) and a solution of HCl in ethyl ether (15% w/v) (1 ml) were added.

Evaporation of the solvents under reduced pressure gave a crude which was purified by chromatography (eluent $CH_2Cl_2:CH_3OH:HCOOH$ 50%=85:15:1).

The resultant solid was dissolved in absolute ethanol, the solution was acidified up to pH 1 by adding a solution of HCl in ethyl ether (15% w/v) and the solvents were removed under reduced pressure.

Crystallization from methanol gave Intermediate 59 (1.4 g) as a white solid.

$^1$H-NMR (200 MHz; DMSO-$d_6$): $\delta$(ppm): 0.91 (t, 3H); 1.20–2.34 (m, 12H); 2.51–3.30 (m, 14H); 3.42–3.67 (m, 1H); 4.93 (s, 2H); 5.16 (s, 2H); 6.86 (d, 1H); 7.02 (d, 1H); 7.17–7.23 (m, 2H); 7.25–7.50 (m, 10H); 7.51–7.59 (m, 2H); 8.69–8.90 (bs, 2H); 9.81–9.98 (bs, 1H).

Mass (thermospray): 685 [M+1].

EXAMPLE 30

Preparation of (S)-N-propyl-N-[5,6-di(phenylmethoxy)-1,2,3,4-tetrahydro-2-naphthyl]-N'-phenylmethoxycarbonyl-N'-[2-(4-methoxycarbonylphenyl)ethyl]-1,6-hexanediamine (Intermediate 60)

Benzylchloroformate (0.8 g; 4.7 mmoles) was added dropwise at room temperature to a stirred solution of Intermediate 57 (2.7 g; 4.1 mmoles), prepared as described in example 27, and triethylamine (0.5 g; 5.0 mmoles) in $CH_2Cl_2$ (70 ml).

The mixture was stirred at room temperature for 1 hour, then an aqueous solution of HCl 1N (20 ml) was added.

The phases were separated and the organic phase was washed with an aqueous solution of $KHCO_3$ 10% (20 ml), dried on $Na_2SO_4$ and the solvent removed under reduced pressure.

Intermediate 60 (3.1 g) was obtained as an amorphous solid.

$^1$H-NMR (200 MHz; $CDCl_3$): $\delta$(ppm): 0.86 (t, 3H); 1.16–2.07 (m, 12H); 2.37–3.51 (m, 15H); 3.89 (s, 3H); 4.99 (s, 2H); 5.09 (s, 2H); 5.08 and 5.12 (2s, 2H); 6.77 (d, 1H); 6.81 (d, 1H); 7.08–7.48 (m, 17H); 7.90–7.98 (m, 2H).

Mass (thermospray): 797 [M+1].

By working in a similar way the following compounds were prepared.

(S)-N-propyl-N-[5,6-di(phenylmethoxy)-1,2,3,4-tetrahydro-2-naphthyl]-N'-phenylmethoxycarbonyl-N'-[2-(4-nitrophenyl)ethyl]-1,6-hexanediamine (Intermediate 61) starting from Intermediate 37.

$^1$H-NMR (200 MHz; CDCl$_3$; 60° C.): δ(ppm): 0.87 (t, 3H); 1.21–2.22 (m, 12H); 2.38–3.23 (m, 13H); 3.48 (t, 2H); 5.00 (s, 2H); 5.09 (2s, 4H); 6.73 (d, 1H); 6.81 (d, 1H); 7.19–7.45 (m, 17H); 8.02–8.11 (m, 2H).

Mass: 784 [M+1].

(S)-N-propyl-N-[5,6-di-(phenylmethoxy)-1,2,3,4-tetrahydro-2-naphthyl]-N'-phenylmethoxycarbonyl-N'-[2-(4-sulphophenyl)ethyl]-1,6-hexanediamine (Intermediate 62) starting from Intermediate 59.

$^1$H-NMR (200 MHz; CDCl$_3$; 60° C.): δ(ppm): 0.32–2.02 (m, 15H); 2.20–3.75 (m, 15H); 5.01 (s, 2H); 5.09 (s, 2H); 5.17 (s, 2H); 6.75–6.91 (m, 2H); 7.00–7.11 (m, 2H); 7.24–7.46 (m, 15H); 7.72–7.83 (m, 2H); 10.25–10.50 (bs, 1H).

Mass (thermospray): 819 [M+1].

EXAMPLE 31

Preparation of (S)-N-propyl-[5,6-di(phenylmethoxy)-1,2,3,4-tetrahydro-2-naphthyl]-N'-phenylmethoxycarbonyl-N'-[2-(4-carbamoylphenyl)ethyl]-1,6-hexanediamine (Intermediate 63)

Aqueous NaOH 32% (3 ml) was added dropwise at room temperature to a stirred solution of Intermediate 60 (3.1 g; 3.9 mmoles), prepared as described in example 30, in dioxane (30 ml) and methanol (3 ml).

The reaction mixture was heated to 80° C. and kept under stirring for 1 hour.

The solvents were removed under reduced pressure, then ethyl acetate (50 ml), water (30 ml) and concentrated HCl up to pH 1 were added. The aqueous phase was extracted with ethyl acetate (20 ml), then the organic phases were collected, washed with water and dried on Na$_2$SO$_4$.

Removal of the solvent under reduced pressure gave a residue which was dissolved in CH$_2$Cl$_2$ (40 ml).

Thionyl chloride (0.6 g; 5.0 mmoles) was added under nitrogen to the stirred solution at room temperature.

After 1 hour at room temperature the reaction mixture was evaporated to dryness under reduced pressure.

The resultant residue was dissolved in CH$_2$Cl$_2$ (10 ml) and the solution was added dropwise under nitrogen to a stirred solution of ammonia in THF 0.65M (80 ml).

The solvents were removed tinder reduced pressure, then CH$_2$Cl$_2$ (40 ml) and water (20 ml) were added.

The organic phase was washed with water and dried on Na$_2$SO$_4$.

The residue was purified by chromatography (eluent CH$_2$Cl$_2$:CH$_3$OH: NH$_4$OH 30%=90:10:0.5) obtaining Intermediate 63 (2.5 g) as an amorphous solid.

$^1$H-NMR (200 MHz; CDCl$_3$): δ(ppm): 0.96 (t, 3H); 1.15–2.07 (m, 12H); 2.36–3.51 (m, 15H); 4.99 (s, 2H); 5.09 (s, 2H); 5.08 and 5.11 (2s, 2H); 5.56–6.28 (bs, 2H); 6.77 (d, 1H); 6.81 (d, 1H); 7.08–7.47 (m, 17H); 7.61–7.77 (m, 2H).

Mass: 782 [M+1].

EXAMPLE 32

Preparation of (S)-N-propyl-[5,6-di(phenylmethoxy)-1,2,3,4-tetrahydro-2-naphthyl]-N'-phenylmethoxycarbonyl-N'-[2-(4-aminophenyl)ethyl]-1,6-hexanediamine (Intermediate 64)

Iron powder (0.65 g) was added in 30 minutes to a stirred suspension of Intermediate 61 (1.1 g; 1.4 mmoles), prepared as described in example 30, in water (6 ml) and acetic acid (0.3 ml) under reflux.

The reaction mixture was heated under reflux for 6 hours, then water (10 ml) and ethyl acetate (30 ml) were added.

The mixture was filtered on Celite® and the phases were separated.

The organic phase was washed with water and then with an aqueous solution of KHCO$_3$, dried on Na$_2$SO$_4$ and the solvent was evaporated under reduced pressure.

The residue was purified by chromatography (eluent CH$_2$Cl$_2$:CH$_3$OH=9:1) obtaining Intermediate 64 (0.7 g) as an oil.

$^1$H-NMR (200 MHz; CDCl$_3$): δ(ppm): 0.87 (t, 3H); 1.12–2.07 (m, 12H); 2.37–3.46 (m, 17H); 4.99 (s, 2H); 5.09 (s, 2H); 5.10 (bs, 2H); 6.52–6.64 (m, 2H); 6.77 (d, 1H); 6.81 (d, 1H); 6.82–7.03 (m, 2H); 7.26–7.48 (m, 15H).

Mass: 754 [M+1].

EXAMPLE 33

Preparation of (S)-N-propyl-[5,6-di(phenylmethoxy)-1,2,3,4-tetrahydro-2-naphthyl]-N'-phenylmethoxycarbonyl-N'-[2-(4-acetylaminophenyl)ethyl]-1,6-hexanediamine (Intermediate 65)

Acetyl chloride (0.08 g; 1.0 moles) was added dropwise at room temperature to a stirred solution of Intermediate 64 (0.7 g; 0.9 mmoles), prepared as described in example 32, and triethylamine (0.14 g; 1.4 mmoles) in CH$_2$Cl$_2$ (7 ml) under nitrogen.

After 2 hours water (10 ml) and CH$_2$Cl$_2$ (10 ml) were added; the phases were separated and the organic phase was dried on Na$_2$SO$_4$.

The solvent was evaporated under reduced pressure obtaining Intermediate 65 (0.7 g) as an oil.

$^1$H-NMR (200 MHz; CDCl$_3$): δ(ppm): 0.89 (t, 3H); 1.13–2.12 (m, 12H); 2.02 and 2.09 (2s, 3H); 2.36–3.53 (m, 15H); 5.01 (s, 2H); 5.10 (s, 2H); 5.11 and 5.15 (2s, 2H); 6.79 (d, 1H); 6.83 (d, 1H); 6.97–7.20 (m, 2H); 7.23–7.49 (m, 17H); 7.95–8.09 (bs, 1H).

Mass: 796 [M+1].

EXAMPLE 34

Preparation of (S)-N-propyl-[5,6-di(phenylmethoxy)-1,2,3,4-tetrahydro-2-naphthyl]-N'-phenylmethoxycarbonyl-N'-[2-(4-methylsulphonylaminophenyl)ethyl]-1,6-hexanediamine (Intermediate 66)

Methanesulphonic anhydride (0.7 g; 4.0 mmoles) was added dropwise at 0° C. to a stirred solution of Intermediate 64 (3.0 g; 4.0 mmoles), prepared as described in example 32, and triethylamine (0.4 g; 4.0 mmoles) in CH$_2$Cl$_2$ (50 ml) under nitrogen.

The reaction mixture was heated at 40° C. and kept under stirring for 2 hours, then cooled to 0° C. and methanesulphonic anhydride (0.35 g; 2.0 moles) was added again.

The reaction mixture was heated at 40° C. and kept under stirring for 2 hours, then water (25 ml) was added and the phases were separated.

The organic phase was dried on Na$_2$SO$_4$ and the solvent was evaporated under reduced pressure.

The residue was purified by chromatography (eluent CH$_2$Cl$_2$:CH$_3$OH:NH$_4$OH 30%=95:5:0.5) obtaining Intermediate 66 (3.1 g) as an oil.

$^1$H-NMR (200 MHz; CDCl$_3$): δ(ppm): 0.87 (t, 3H); 1.11–2.08 (m, 12H); 2.33–3.49 (m, 15H); 2.93 (s, 3H); 4.99

(s, 2H); 5.10 (s, 2H); 5.10 and 5.12 (2s, 2H); 6.76 (d, 1H); 6.81 (d, 1H); 7.00–7.21 (m, 4H); 7.25–7.47 (m, 15H).

Mass: 832 [M+1].

EXAMPLE 35

Preparation of (S)-N-propyl-[5,6-di(phenylmethoxy)-1,2,3,4-tetrahydro-2-naphthyl]-N'-phenylmethoxycarbonyl-N'-[2-(4-aminocarbonylaminophenyl)ethyl]-1,6-hexanediamine (Intermediate 67)

Concentrated HCl (0.7 g; 7.1 mmoles) and sodium cyanate (0.38 g; 5.8 mmoles) were added at room temperature to a stirred solution of Intermediate 64 (2.2 g; 2.9 mmoles), prepared as described in example 32, in chlorobenzene (20 ml) under nitrogen.

The reaction mixture was heated at 110° C. and kept under stirring for 1 hour.

The solvents were removed under reduced pressure, then water (30 ml) and ethyl acetate (50 ml) were added.

The phases were separated, the organic phase was dried on $Na_2SO_4$ and the solvent was removed under reduced pressure.

The residue was purified by chromatography (eluent $CH_2Cl_2$:$CH_3OH$:$NH_4OH$ 30%=90:10:0.5) obtaining Intermediate 67 (1.9 g) as an oil.

$^1$H-NMR (200 MHz; $CDCl_3$): δ(ppm): 0.91 (t, 3H); 1.01–2.22 (m, 12H); 2.44–3.48 (m, 15H); 4.99 (s, 2H); 5.06 (bs, 2H); 5.10 (2s, 4H); 6.76 (d, 1H); 6.81 (d, 1H); 6.89–7.11 (m, 2H); 7.20–7.46 (m, 17H); 7.81–8.08 (bs, 1H).

Mass: 797 [M+1].

EXAMPLE 36

Preparation of (S)-N-propyl-N-[6-[2-(4-methylsulphonylphenyl)ethylamino]hexyl]-5,6-dimethoxy-1,2,3,4-tetrahydro-2-naphthylamine dihydrochloride (Intermediate 68)

1,1'-carbonyldiimidazole (0.76 g; 4.7 mmoles) was added to a stirred suspension of (4-methylsulphonyl)phenylacetic acid (1.0 g; 4.7 mmoles), prepared as described in J. Chem. Soc., 1501–6 (1948), in $CH_2Cl_2$ (25 ml).

The mixture was kept under stirring for 1.5 hours at room temperature, then triethylamine (0.48 g; 4.7 mmoles) and a solution of Intermediate 24 (1.7 g; 4.7 mmoles), prepared as described in example 11, in $CH_2Cl_2$ (20 ml) were added.

After 1 hour water (30 ml) and $CH_2Cl_2$ (30 ml) were added; the phases were separated and the organic phase was dried on $Na_2SO_4$.

The solvent was removed under reduced pressure and the residue was dissolved under nitrogen in anhydrous THF (25 ml).

Borane-dimethylsulphide complex (2.1 g; 26.6 mmoles) was slowly added at room temperature under stirring.

The reaction mixture was heated under reflux for 1.5 hours.

After cooling to 5° C., a solution of concentrated HCl (1.1 ml) in methanol (11 ml) was slowly added.

The mixture was heated under reflux for 1 hour, concentrated by distilling the solvents at atmospheric pressure and then under reduced pressure up to dryness.

The residue was dissolved in methanol (30 ml); the solvent was distilled off under reduced pressure, methanol (30 ml) was added and the solvent was removed again.

Absolute ethanol (30 ml) and a solution of HCl in ethyl ether (15% w/v) (1 ml) were added; evaporation of the solvents under reduced pressure gave a crude which was purified by chromatography (eluent $CH_2Cl_2$:$CH_3OH$:HCOOH 50%=85:15:1).

The resultant solid was dissolved in absolute ethanol and the solution was acidified to pH 1 by adding a solution of HCl in ethyl ether (15% w/v).

Evaporation of the solvents under reduced pressure gave Intermediate 68 (2.3 g) as a white amorphous solid.

$^1$H-NMR (200 MHz; $D_2O$): δ(ppm): 0.83 (t, 3H); 1.16–2.25 (m, 12H); 2.47–3.28 (m, 14H); 3.11 (s, 3H); 3.49–3.68 (m, 1H); 3.61 (s, 3H); 3.70 (s, 3H); 6.84 (s, 2H); 7.40–7.48 (m, 2H); 7.75–7.83 (m, 2H).

Mass (thermospray): 531 [M+1].

EXAMPLE 37

Preparation of (S)-N-propyl-[5,6-di(phenylmethoxy)-1,2,3,4-tetrahydro-2-naphthyl]-N'-phenylmethoxycarbonyl-N'-[2-(4-sulphamoylphenyl)ethyl] -1,6-hexanediamine (Intermediate 69)

DMF (15 µl) and thionyl chloride (0.65 g; 5.5 mmoles) were added at room temperature to a stirred solution of Intermediate 59 (3.0 g; 3.7 mmoles), prepared as described in example 29, in toluene (60 ml) under nitrogen.

The reaction mixture was heated at 80° C. and kept under stirring for 4 hours, then the solvent was removed under reduced pressure.

The residue was dissolved in THF (30 ml) and the solution was added dropwise, at 0° C. under nitrogen, to a 0.65M solution of ammonia in THF (28 ml).

The reaction mixture was allowed to heat spontaneously up to room temperature overnight, then the solvent was removed under reduced pressure and water (30 ml) and $CH_2Cl_2$ (50 ml) were added to the residue.

The phases were separated, the organic phase was dried on $Na_2SO_4$ and the solvent was removed under reduced pressure.

The residue was purified by chromatography (eluent $CH_2Cl_2$:$CH_3OH$=95:5) obtaining Intermediate 69 (1.6 g) as an oil.

$^1$H-NMR (200 MHz; $CDCl_3$): δ(ppm): 0.89 (t, 3H); 1.08–2.12 (m, 14H); 2.33–3.53 (m, 15H); 4.99 (s, 2H); 5.09 (2s, 4H); 6.76 (d, 1H); 6.81 (d, 1H); 7.11–7.23 (m, 2H); 7.25–7.48 (m, 15H); 7.71–7.85 (m, 2H).

Mass (thermospray): 818 [M+1].

EXAMPLE 38

Preparation of (S)-N-propyl-N-[6-[(1,4-benzodioxan-2-yl)methylamino]hexyl]-5,6-dihydroxy-1,2,3,4-tetrahydro-2-naphthylamine dihydrochloride (Compound 1)

By working in a way similar to that described in example 20 but by using Intermediate 5 instead of Intermediate 2, Compound 1 was obtained.

$^1$H-NMR (200 MHz; $D_2O$): δ(ppm): 0.80 (t, 3H); 1.18–1.68 (m, 10H); 1.63–2.20 (m, 2H); 2.38–3.27 (m, 12H); 3.42–3.60 (m, 1H); 3.95 (dd, 1H); 4.18 (dd, 1H); 4.44–4.54 (m, 1H); 6.50 (d, 1H); 6.62 (d, 1H); 6.75–6.85 (m, 4H).

Mass (chemical ionization ammonia positive ions): 469 [M+1].

Similarly, the following compounds were obtained.

(S)-N-propyl-N-[6-[2-(3,4-methylendioxyphenyl)ethylamino]hexyl]-5,6-dihydroxy-1,2,3,4-tetrahydro-2-naphthylamine dihydrochloride (Compound 2) starting from Intermediate 4.

$^1$H-NMR (200 MHz; D$_2$O): δ(ppm): 0.83 (t, 3H); 1.21–2.19 (m, 12H); 2.40–3.15 (m, 14H); 3.43–3.60 (m, 1H); 5.79 (s, 2H); 6.49–6.73 (m, 5H).

Mass: 469 [M+1].

(S)-N-propyl-N-[6-[4-(2-methoxyphenyl)piperazin-1-yl] hexyl]-5,6-dihydroxy-1,2,3,4-tetrahydro-2-naphthylamine trihydrochloride (Compound 3) starting from Intermediate 12.

$^1$H-NMR (200 MHz; D$_2$O): δ(ppm): 0.79 (t, 3H); 1.22–1.78 (m, 10H); 1.52–2.18 (m, 2H); 2.37–3.64 (m, 19H); 3.69 (s, 3H); 6.48 (d, 1H); 6.60 (d, 1H); 6.80–7.09 (m, 4H).

Mass (thermospray): 496 [M+1].

(S)-N-propyl-N-[6-[2-(2-nitrophenoxy)ethylamino]hexyl]-5,6-dihydroxy-1,2,3,4-tetrahydro-2-naphthylamine dihydrochloride (Compound 4) starting from Intermediate 7.

$^1$H-NMR (200 MHz; D$_2$O): δ(ppm): 0.80 (t, 3H); 1.23–2.19 (m, 12H); 2.36–3.11 (m, 10H); 3.33–3.58 (m, 3H); 4.29–4.34 (m, 2H); 6.46 (d, 1H); 6.58 (d, 1H); 6.96–7.74 (m, 4H).

Mass: 486 [M+1].

(S)-N-propyl-N-[6-[2-(4-nitrophenoxy)ethylamino]hexyl]-5,6-dihydroxy-1,2,3,4-tetrahydro-2-naphthylamine dihydrochloride (Compound 5) starting from Intermediate 8.

$^1$H-NMR (200 MHz; D$_2$O): δ(ppm): 0.80 (t, 3H) 1.21–1.68 (m, 10H); 1.62–2.15 (m, 2H); 2.34–3.08 (m, 10H); 3.33–3.38 (m, 2H); 3.40–3.56 (m, 1H) 4.23–4.27 (m, 2H); 6.45 (d, 1H); 6.58 (d, 1H); 6.88–8.06 (m, 4H).

Mass: 486 [M+1].

(S)-N-propyl-N-[6-[2-(4-methylsulphonylphenoxy) ethylamino]hexyl]-5,6-dihydroxy-1,2,3,4-tetrahydro-2-naphthylamine dihydrochloride (Compound 6) starting from Intermediate 9.

$^1$H-NMR (200 MHz; D$_2$O): δ(ppm): 0.84 (t, 3H); 1.30–2.21 (m, 12H); 2.42–3.16 (m, 10H); 3.10 (s, 3H); 3.38–3.42 (m, 2H); 3.47–3.63 (m, 1H); 4.26–4.31 (m, 2H); 6.53 (d, 1H); 6.66 (d, 1H); 7.05–7.80 (m, 4H).

Mass (chemical ionization, ammonia, positive ions): 519 [M+1].

EXAMPLE 39

Preparation of (S)-N-propyl-N-[6-[(2-methoxyphenoxy) acetylamino]hexyl]-5,6-dihydroxy-1,2,3,4-tetrahydro-2-naphthylamine hydrochloride (Compound 7)

DMF (2 drops) and thionyl chloride (0.6 g; 5 mmoles) were added to a suspension of (2-methoxyphenoxy)acetic acid (0.6 g; 3.3 mmoles), prepared as described in Cesk. Farm. 1968, 17(1), 28–33 (Chemical Abstracts 69:67041 g), in CH$_2$Cl$_2$ (10 ml), under nitrogen at room temperature.

After 3 hours the solvent was evaporated under reduced pressure obtaining an oil which was dissolved in CH$_2$Cl$_2$ (5 ml).

Sodium tetraborate (1 g; 5 mmoles) was added under nitrogen to a solution of Intermediate 26 (1.2 g; 2.5 moles), prepared as described in example 13, in water (15 ml).

After heating at 70° C. up to complete dissolution and cooling at room temperature, CH$_2$Cl$_2$ (2 ml), potassium carbonate (2.7 g; 19.5 mmoles) and, under vigorous stirring, the above prepared solution in CH$_2$Cl$_2$ were added.

After 1 hour at room temperature, the reaction mixture was acidified with HCl 37% up to pH 1 and the phases were separated.

The aqueous phase was extracted with CH$_2$Cl$_2$ (15 ml). The collected organic phases were washed with brine slightly acidified by HCl, dried on Na$_2$SO$_4$ and brought to dryness under reduced pressure.

The resultant residue was purified by chromatography (eluent CH$_2$Cl$_2$:CH$_3$OH:HCOOH 50%=85:15:1).

The resultant solid was dissolved in absolute ethanol.

After addition of a solution of HCl in ethyl ether (15% w/v) up to a clearly acid pH, the solvents were evaporated under reduced pressure obtaining Compound 7 (0.9 g) as an amorphous white solid.

$^1$H-NMR (200 MHz; D$_2$O): δ(ppm): 0.79 (t, 3H); 0.96–2.09 (m, 12H); 2.28–3.10 (m, 10H); 3.26–3.42 (m, 1H); 3.63 (m, 3H); 4.35 and 4.36 (2s, 2H); 6.43 (d, 1H); 6.58 (d, 1H); 6.64–6.80 (m, 4H).

Mass: 485 [M+1].

EXAMPLE 40

Preparation of (S)-N-propyl-N-[6-[2-(4-hydroxyphenylthio) ethylamino]hexyl]-5,6-dihydroxy-1,2,3,4-tetrahydro-2-naphthylamine dihydrobromide (Compound 8)

A solution of Intermediate 33 (1.9 g; 3.2 mmoles), prepared as described in example 18, in 48% HBr (19 ml) was heated under reflux under nitrogen for 5 hours.

The reaction mixture was then brought to dryness under reduced pressure and absolute ethanol (40 ml) was added to the resultant residue.

After evaporation of the solvent and addition of ethyl acetate (40 ml), the solvent was evaporated again.

The resultant residue was purified by chromatography (eluent CH$_2$Cl$_2$:CH$_3$OH:HCOOH 50%=85:15:1) obtaining Compound 8 (0.8 g) as an amorphous white solid.

$^1$H-NMR (200 MHz; D$_2$O): δ(ppm): 0.78 (t, 3H); 1.17–2.14 (m, 12H); 2.35–3.06 (m, 14H); 3.38–3.56 (m, 1H); 6.46 (d, 1H); 6.58 (d, 1H); 6.65–7.26 (m, 4H).

Mass: 473 [M+1].

By working in a similar way the following compounds were prepared.

(S)-N-propyl-N-[6-[3-(4-hydroxyphenyl)propylamino] hexyl]-5,6-dihydroxy-1,2,3,4-tetrahydro-2-naphthylamine dihydrobromide (Compound 9) starting from Intermediate 34.

$^1$H-NMR (200 MHz; D$_2$O): δ(ppm): 0.80 (t, 3H); 1.15–2.15 (m, 14H); 2.33–3.11 (m, 14H); 3.34–3.51 (m, 1H); 6.45 (d, 1H); 6.59 (d, 1H); 6.63–6.98 (m, 4H).

Mass: 455 [M+1].

(S)-N-propyl-N-[6-(6,7-dihydroxy-1,2,3,4-tetrahydroisoquinolin-2-yl)hexyl]-5,6-dihydroxy-1,2,3,4-tetrahydro-2-naphthylamine dihydrobromide (Compound 10) starting from Intermediate 35.

$^1$H-NMR (200 MHz; D$_2$O): δ(ppm): 0.82 (t, 3H); 1.28–2.16 (m, 12H); 2.38–3.59 (m, 15H); 4.08 (bs, 2H); 6.49 and 6.57 (2s, 2H); 6.49 (d, 1H); 6.61 (d, 1H).

Mass (thermospray): 469 [M+1].

(S)-N-propyl-N-[6-[2-(3-chloro-4-hydroxyphenyl) ethylamino]hexyl]-5,6-dihydroxy-1,2,3,4-tetrahydro-2-naphthylamine dihydrobromide (Compound 11) starting from Intermediate 42.

$^1$H-NMR (200 MHz; D$_2$O): δ(ppm): 0.82 (t, 3H); 1.19–2.19 (m, 12H); 2.38–3.14 (m, 14H); 3.42–3.57 (m, 1H); 6.49 (d, 1H); 6.62 (d, 1H); 6.80 (d, 1H); 6.94 (dd, 1H); 7.15 (d, 1H).

Mass: 475 [M+1].

(S)-N-propyl-N-[6-[2-(3-nitro-4-hydroxyphenyl) ethylamino]hexyl]-5,6-dihydroxy-1,2,3,4-tetrahydro-2-naphthylamine dihydrobromide (Compound 12) starting from Intermediate 43.

$^1$H-NMR (200 MHz; D$_2$O): δ(ppm): 0.82 (t, 3H); 1.17–2.25 (m, 12H); 2.40–3.23 (m, 14H); 3.47–3.65 (m, 1H); 6.52 (d, 1H); 6.64 (d, 1H); 6.83–7.10 (m, 3H).

(S)-N-propyl-N-[6-[3-(3,4-dihydroxyphenyl)propylamino]hexyl]-5,6-dihydroxy- 1,2,3,4-tetrahydro-2-naphthylamine dihydrobromide (Compound 13) starting from Intermediate 45.

¹H-NMR (200 MHz; D₂O): δ(ppm): 0.81 (t, 3H); 1.17–2.17 (m, 14H); 2.42 (t, 2H) 2.37–3.10 (m, 12H); 3.44–3.60 (m, 1H); 6.48–6.71 (m, 5H).

Mass (thermospray): 471 [M+1].

(S)-N-propyl-N-[6-[2-(3-methyl-4-hydroxyphenyl)ethylamino]hexyl]-5,6-dihydroxy-1,2,3,4-tetrahydro-2-naphthylamine dihydrobromide (Compound 14) starting from Intermediate 46.

¹H-NMR (200 MHz; D₂O): δ(ppm): 0.82 (t, 3H); 1.20–2.19 (m, 12H); 2.02 (s, 3H); 2.40–3.13 (m, 14H); 3.44–3.60 (m, 1H); 6.51 (d, 1H); 6.64 (d, 1H) 6.67–6.95 (m, 3H).

Mass (thermospray): 455 [M+1].

(S)-N-propyl-N-[6-[4-(4-hydroxyphenylmethyl)piperazin-1-yl]hexyl]-5,6-dihydroxy-1,2,3,4-tetrahydro-2-naphthylamine trihydrobromide (Compound 15) starting from Intermediate 49.

¹H-NMR (200 MHz; D₂O): δ(ppm): 0.80 (t, 3H); 1.20–2.20 (m, 12H); 2.39–3.15 (m, 10H); 3.35–3.59 (m, 9H); 4.19 (s, 2H); 6.50 (d, 1H); 6.62 (d, 1H); 6.76–7.25 (m, 4H).

Mass (chemical ionization, ammonia, positive ions): 496 [M+1].

(S)-N-propyl-N-[6-[3-(2-hydroxyphenyl)propylamino]hexyl]-5,6-dihydroxy-1,2,3,4-tetrahydro-2-naphthylamine dihydrobromide (Compound 16) starting from Intermediate 40.

¹H-NMR (200 MHz; D₂O): δ(ppm): 0.79 (t, 3H); 1.18–2.18 (m, 14H); 2.48–2.55 (m, 2H); 2.38–3.09 (m, 12H); 3.43–3.60 (m, 1H); 6.49 (d, 1H); 6.61 (d, 1H); 6.71–7.05 (m, 4H).

Mass: 455 [M+1].

(S)-N-propyl-N-[6-[2-(3,5-dihydroxy-4-methylphenyl)ethylamino]hexyl]-5,6-dihydroxy-1,2,3,4-tetrahydro-2-naphthylamine dihydrobromide (Compound 17) starting from Intermediate 47.

¹H-NMR (200 MHz; D₂O): δ(ppm): 0.85 (t, 3H); 1.20–2.24 (m, 12H); 1.90 (s, 3H); 2.44–3.17 (m, 14H); 3.48–3.63 (m, 1H); 6.29 (s, 2H); 6.55 (d, 1H); 6.67 (d, 1H).

Mass: 471 [M+1].

(S)-N-propyl-N-[6-[2-(2-oxo-3H-1,3-benzothiazol-6-yl)ethylamino]hexyl]-5,6-dihydroxy-1,2,3,4-tetrahydro-2-naphthylamine dihydrobromide (Compound 18) starting from Intermediate 50.

¹H-NMR (200 MHz; D₂O): δ(ppm): 0.80 (t, 3H); 1.17–2.17 (m, 12H); 2.34–3.18 (m, 14H); 3.38–3.54 (m, 1H); 6.45 (d, 1H); 6.58 (d, 1H); 6.96–7.24 (m, 3H).

Mass: 498 [M+1].

(S)-N-propyl-N-[6-[2-(2-oxo-3H-1,3-benzothiazol-5-yl)ethylamino]hexyl]-5,6-dihydroxy-1,2,3,4-tetrahydro-2-naphthylamine dihydrobromide (Compound 19) starting from Intermediate 51.

¹H-NMR (200 MHz; D₂O; 60° C.): δ(ppm): 1.20 (t, 3H); 1.60–2.56 (m, 12H); 2.78–3.61 (m, 14H); 3.83–3.96 (m, 1H); 6.90 (d, 1H); 7.02 (d, 1H); 7.35–7.40 (m, 2H); 7.75 (d, 1H).

Mass: 498 [M+1].

(S)-N-propyl-N-[6-[2-(2-oxo-3H-1,3-benzothiazol-6-yl)ethylamino]hexyl]-5-hydroxy-1,2,3,4-tetrahydro-2-naphthylamine dihydrobromide (Compound 20) starting from Intermediate 54.

¹H-NMR (200 MHz; DMSO-d₆): δ(ppm): 0.93 (t, 3H); 1.20–2.31 (m, 12H); 2.84–3.25 (m, 14H); 3.56–3.71 (m, 1H); 6.55–7.48 (m, 6H); 8.50 (bs, 2H); 9.14 (bs, 1H); 9.40 (bs, 1H).

Mass: 482 [M+1].

(S)-N-propyl-N-[6-[2-(3-chloro-5-hydroxyphenyl)ethylamino]hexyl]-5,6-dihydroxy-1,2,3,4-tetrahydro-2-naphthylamine dihydrobromide (Compound 21) starting from Intermediate 53.

¹H-NMR (200 MHz; D₂O): δ(ppm): 0.79 (t, 3H) 1.18–2.17 (m, 12H); 2.38–3.15 (m, 14H); 3.44–3.59 (m, 1H); 6.48 (d, 1H); 6.61 (d, 1H); 6.54–6.72 (m, 3H).

(S)-N-propyl-N-[6-[2-(4-methylsulphonylphenyl)ethylamino]hexyl]-5,6-dihydroxy-1,2,3,4-tetrahydro-2-naphthylamine dihydrobromide (Compound 22) starting from Intermediate 68.

¹H-NMR (200 MHz; D₂O): δ(ppm): 0.79 (t, 3H); 1.11–2.14 (m, 12H); 2.36–3.21 (m, 14H); 3.07 (s, 2H); 3.39–3.56 (m, 1H); 6.48 (d, 1H); 6.60 (d, 1H); 7.36–7.77 (m, 4H).

Mass (thermospray): 503 [M+1].

(S)-N-propyl-N-[6-(2,3-dihydro-indol-1-yl)hexyl]-5,6-dihydroxy-1,2,3,4-tetrahydro-2-naphthylamine dihydrobromide (Compound 23) starting from Intermediate 36.

¹H-NMR (200 MHz; D₂O): δ(ppm): 0.85 (t, 3H); 1.27–2.22 (m, 12H); 2.43–3.61 (m, 13H); 3.83 (t, 2H) 6.54 (d, 1H); 6.67 (d, 1H); 7.33–7.39 (m, 4H).

Mass: 423 [M+1].

EXAMPLE 41

Preparation of (S)-N-propyl-N-[6-[2-(4-hydroxyphenoxy)ethylamino]hexyl]-5,6-dihydroxy-1,2,3,4-tetrahydro-2-naphthylamine dihydrochloride (Compound 24)

HCl 37% (1 ml) and Pd on charcoal 10% (50% water) (0.7 g) were added to a solution of Intermediate 38 (3.4 g; 5.5 mmoles), prepared as described in example 20, in absolute ethanol (100 ml).

The mixture was hydrogenated in Parr apparatus (2.7 atm) for 3 hours.

The catalyst was filtered and the solution was brought to dryness under reduced pressure.

The residue was purified by chromatography (eluent CH₂Cl₂:CH₃OH:HCOOH 50%=85:15:2).

The resultant solid was dissolved in absolute ethanol (40 ml). After addition of a solution of HCl in ethyl ether (15% w/v) up to clearly acid pH and evaporation of the solvents under reduced pressure, Compound 24 (2.5 g) was obtained as an amorphous white solid.

¹H-NMR (200 MHz; D₂O): δ(ppm): 0.83 (t, 3H); 1.22–2.16 (m, 12H); 2.39–3.13 (m, 10H); 3.27–3.32 (m, 2H); 3.42–3.57 (m, 1H); 4.06–4.11 (m, 2H); 6.50 (d, 1H); 6.64 (d, 1H); 6.65–6.80 (m, 4H).

Mass (thermospray): 457 [M+1].

By working in a similar way the following compounds were prepared.

(S)-N-propyl-N-[6-[2-(3,4-dihydroxyphenyl)ethoxy]hexyl]-5,6-dihydroxy-1,2,3,4-tetrahydro-2-naphthylamine hydrochloride (Compound 25) starting from Intermediate 39.

¹H-NMR (200 MHz; DMSO-d₆): δ(ppm): 0.91 (t, 3H); 1.29–2.32 (m, 12H); 2.60 (t, 2H); 2.42–3.20 (m, 8H); 3.35 (t, 2H); 3.45 (t, 2H); 3.40–3.60 (m, 1H); 6.38–6.63 (m, 5H); 8.31 and 8.67 and 8.73 and 9.08 (4s, 4H); 10.05 (bs, 1H).

Mass (thermospray): 458 [M+1].

(S)-N-propyl-N-[6-[2-(3-methoxy-4-hydroxyphenyl)ethylamino]hexyl]-5,6-dihydroxy-1,2,3,4-tetrahydro-2-naphthylamine dihydrochloride (Compound 26) starting form Intermediate 44.

¹H-NMR (200 MHz; D₂O): δ(ppm): 0.83 (t, 3H); 1.20–2.20 (m, 12H); 2.42–3.17 (m, 14H); 3.46–3.65 (m, 1H); 3.71 (s, 3H); 6.50–6.82 (m, 5H).

Mass: 471 [M+1].

(S)-N-propyl-N-[6-[2-(3-hydroxy-4-methoxyphenyl)
ethylamino]hexyl]-5,6-dihydroxy-1,2,3,4-tetrahydro-2-
naphthylamine dihydrochloride (Compound 27) starting
from Intermediate 48.

$^1$H-NMR (200 MHz; D$_2$O): δ(ppm): 0.80 (t, 3H);
1.16–2.18 (m, 12H); 2.38–3.11 (m, 14H); 3.43–3.59 (m,
1H); 3.66 (s, 3H); 6.49 (d, 1H); 6.62 (d, 1H); 6.64–6.86 (m,
3H).

Mass: 471 [M+1].

(S)-N-propyl-N-[6-[2-(3,4-dihydroxyphenyl)ethylthio]
hexyl]-5,6-dihydroxy-1,2,3,4-tetrahydro-2-naphthylamine
hydrochloride (Compound 28) starting from Intermediate
41.

$^1$H-NMR (200 MHz; DMSO-d$_6$): δ(ppm): 0.91 (t, 3H);
1.26–2.29 (m, 12H); 2.45–3.22 (m, 14H); 3.46–3.62 (m,
1H); 6.38–6.63 (m, 5H); 8.28 (s, 1H); 8.68 (s, 1H); 8.72 (s,
1H); 9.06 (s, 1H); 9.44 (bs, 1H).

(S)-N-propyl-N-[6-[2-(3-amino-4-hydroxyphenyl)
ethylamino]hexyl]-5,6-dihydroxy-1,2,3,4-tetrahydro-2-
naphthylamine trihydrochloride (Compound 29) starting
from Compound 12.

$^1$H-NMR (200 MHz; D$_2$O): δ(ppm): 0.80 (t, 3H);
1.20–2.20 (m, 12H); 2.39–3.15 (m, 14H); 3.45–3.61 (m,
1H); 6.50 (d, 1H); 6.62 (d, 1H); 6.82–7.05 (m, 3H).

Mass (thermospray): 456 [M+1].

(S)-N-propyl-N-[6-[2-(4-sulphamoylphenyl)ethylamino]
hexyl]-5,6-dihydroxy-1,2,3,4-tetrahydro-2-naphthylamine
dihydrochloride (Compound 30) starting from Intermediate
69.

$^1$H-NMR (200 MHz; D$_2$O): δ(ppm): 0.80 (t, 3H);
1.22–2.16 (m, 12H); 2.38–3.21 (m, 14H); 3.44–3.57 (m,
1H); 6.49 (d, 1H); 6.61 (d, 1H); 7.32–7.72 (m, 4H).

Mass: 504 [M+1].

(S)-N-propyl-N-[6-[2-(4-methylsulphonylaminophenyl)
ethylamino]hexyl]-5,6-dihydroxy-1,2,3,4-tetrahydro-2-
naphthylamine dihydrochloride (Compound 31) starting
from Intermediate 66.

$^1$H-NMR (200 MHz; D$_2$O): δ(ppm): 0.81 (t, 3H);
1.23–2.17 (m, 12H); 2.91 (s, 3H); 2.38–3.17 (m, 14H);
3.44–3.59 (m, 1H); 6.50 (d, 1H); 6.63 (d, 1H); 7.07–7.20 (m,
4H).

Mass (thermospray): 518 [M+1].

(S)-N-propyl-N-[6-[2-(4-aminocarbonylaminophenyl)
ethylamino]hexyl]-5,6-dihydroxy-1,2,3,4-tetrahydro-2-
naphthylamine dihydrochloride (Compound 32) starting
from Intermediate 67.

$^1$H-NMR (200 MHz; D$_2$O): δ(ppm): 0.80 (t, 3H);
1.21–2.15 (m, 12H); 2.36–3.15 (m, 14H); 3.40–3.55 (m,
1H); 6.48 (d, 1H); 6.61 (d, 1H); 7.09 (s, 4H).

Mass (thermospray): 483 [M+1].

(S)-N-propyl-N-[6-[2-(4-acetylaminophenyl)ethylamino]
hexyl]-5,6-dihydroxy-1,2,3,4-tetrahydro-2-naphthylamine
dihydrochloride (Compound 33) starting from Intermediate
65.

$^1$H-NMR (200 MHz; D$_2$O): δ(ppm): 0.80 (t, 3H);
1.21–2.17 (m, 12H); 1.98 (s, 3H); 2.38–3.17 (m, 14H);
3.43–3.60 (m, 1H); 6.49 (d, 1H); 6.62 (d, 1H); 7.11–7.23 (m,
4H).

Mass (thermospray): 482 [M+1].

EXAMPLE 42

Preparation of (S)-N-propyl-N-[6-[(3,4-dihydroxyphenyl)
acetylamino]hexyl]-5,6-dihydroxy-1,2,3,4-tetrahydro-2-
naphthylamine hydrobromide (Compound 34)

A 1M solution of boron tribromide in CH$_2$Cl$_2$ (4.7 ml)
was added to a solution of Intermediate 55 (0.6 g; 1.1
mmoles), prepared as described in example 25, in CH$_2$Cl$_2$ (8
ml), under nitrogen at 0° C.

The reaction mixture was allowed to heat spontaneously
up to room temperature.

After 3 hours at room temperature methanol (5 ml) was
added and the resultant solution was brought to dryness
under reduced pressure.

The crude was purified by chromatography (eluent
CH$_2$Cl$_2$:CH$_3$OH:HCOOH 50%=85:15:1) obtaining Compound 34 (0.6 g) as an amorphous white solid.

$^1$H-NMR (200 MHz; D$_2$O): δ(ppm): 0.81 (t, 3H);
1.10–2.14 (m, 12H); 2.38–3.07 (m, 10H); 3.24 (s, 2H);
3.38–3.53 (m, 1H); 6.48–6.68 (m, 5H).

Mass (thermospray): 471 [M+1].

EXAMPLE 43

Preparation of (S)-N-propyl-N-[6-[2-(4-
methoxycarbonylphenyl)ethylamino]hexyl]-5,6-dihydroxy-
1,2,3,4-tetrahydro-2-naphthylamine dihydrochloride
(Compound 35)

Pd on charcoal 10% (50% water) (0.4 g) was added to a
solution of Intermediate 56 (1.9 g; 2.7 moles), prepared as
described in example 26, in methanol (50 ml).

The mixture was kept under stirring under hydrogen
pressure (2.7 atm) at 40° C. for 6 hours.

The catalyst was filtered off and the solvent was evaporated under reduced pressure.

The residue was dissolved in THF (50 ml) under nitrogen
and borane-dimethylsulphide complex (1.1 g; 13.7 mmoles)
was slowly added at room temperature under stirring.

The reaction mixture was heated under reflux for 2 hours.

After cooling to 5° C., a solution of concentrated HCl (0.5
ml) in methanol (4 ml) was slowly added.

The mixture was heated under reflux for 2 hours, then
concentrated by distilling the solvents at atmospheric pressure and then under reduced pressure up to dryness.

The residue was dissolved in methanol (20 ml); the
solvent was distilled off under reduced pressure, methanol
(20 ml) was added and the solvent was removed again.

Absolute ethanol (20 ml) and a solution of HCl in ethyl
ether (15% w/v) (1 ml) were added; evaporation of the
solvents under reduced pressure gave a crude which was
purified by chromatography (eluent
CH$_2$Cl$_2$:CH$_3$OH:HCOOH 50%=85:15:2).

The resultant solid was dissolved in absolute ethanol and
the solution was acidified to pH 1 by adding a solution of
HCl in ethyl ether (15% w/v).

Evaporation of the solvents under reduced pressure gave
Compound 35 (0.6 g) as a white amorphous solid.

$^1$H-NMR (200 MHz; D$_2$O): δ(ppm): 0.80 (t, 3H);
1.19–2.19 (m, 12H); 2.39–3.22 (m, 14H); 3.43–3.59 (m,
1H); 3.75 (s, 3H); 6.49 (d, 1H); 6.62 (d, 1H); 7.24–7.85 (m,
4H).

Mass: 483 [M+1].

By working in a similar way the following compound was
prepared.

(S)-N-propyl-N-[6-[2-(4-hydroxymethylphenyl)
ethylamino]hexyl]-5,6-dihydroxy-1,2,3,4-tetrahydro-2-
naphthylamine dihydrochloride (Compound 36) starting
from Intermediate 58.

$^1$H-NMR (200 MHz; D$_2$O): δ(ppm): 0.80 (t, 3H);
1.19–2.19 (m, 12H); 2.40–3.18 (m, 14H); 3.45–3.60 (m,
1H); 4.44 (s, 2H); 6.50 (d, 1H); 6.63 (d, 1H); 7.13–7.24 (m,
4H).

Mass: 455 [M+1].

EXAMPLE 44

Preparation of (S)-N-propyl-N-[6-[2-(4-carbamoylphenyl)ethylamino]hexyl]-5,6-dihydroxy-1,2,3,4-tetrahydro-2-naphthylamine dihydrochloride (Compound 37)

Concentrated HCl (0.7 ml) and Pd on charcoal 10% (0.5 g) were added to a solution of Intermediate 63 (2.4 g; 3.1 moles), prepared as described in example 31, in ethanol (70 ml).

The mixture was kept under stirring under hydrogen pressure (2.7 atm) at room temperature for 36 hours.

The catalyst was filtered off and the solvents were evaporated under reduced pressure.

The crude was purified by chromatography (eluent $CH_2Cl_2$:$CH_3OH$:HCOOH 50%=80:20:2).

The resultant solid was dissolved in absolute ethanol and the solution was acidified to pH 1 by adding a solution of HCl in ethyl ether (15% w/v).

Evaporation of the solvents under reduced pressure gave Compound 37 (0.7 g) as a white amorphous solid.

$^1$H-NMR (200 MHz; $D_2O$): δ(ppm): 0.79 (t, 3H); 1.18–2.17 (m, 12H); 2.38–3.20 (m, 14H); 3.43–3.59 (m, 1H); 6.49 (d, 1H); 6.61 (d, 1H); 7.23–7.63 (m, 4H).

Mass (thermospray): 468 [M+1].

EXAMPLE 45

Preparation of (S)-N-propyl-N-[6-[2-(4-carboxyphenyl)ethylamino]hexyl]-5,6-dihydroxy-1,2,3,4-tetrahydro-2-naphthylamine dihydrochloride (Compound 38)

A stirred solution of Compound 35 (1.0 g; 1.8 mmoles), prepared as described in example 43, in dioxane (10 ml) and concentrated HCl (5 ml) was heated under reflux for 6 hours.

The solvents were removed under reduced pressure and the residue was purified by chromatography (eluent $CH_2Cl_2$:$CH_3OH$:HCOOH 50%=80:20:2). The resultant solid was dissolved in absolute ethanol and the solution was acidified to pH 1 by adding a solution of HCl in ethyl ether (15% w/v).

Evaporation of the solvents under reduced pressure gave Compound 38 (0.6 g) as a white amorphous solid.

$^1$H-NMR (200 MHz; $D_2O$): δ(ppm): 0.81 (t, 3H); 1.20–2.20 (m, 12H); 2.40–3.23 (m, 14H); 3.44–3.60 (m, 1H); 6.50 (d, 1H); 6.63 (d, 1H); 7.25–7.84 (m, 4H).

Mass: 469 [M+1].

EXAMPLE 46

Preparation of (S)-N-propyl-N-[6-[2-(4-sulphophenyl)ethylamino]hexyl]-5,6-dihydroxy-1,2,3,4-tetrahydro-2-naphthylamine dihydrochloride (Compound 39)

Concentrated HCl (2 ml) and Pd on charcoal 10% (50% water) (0.6 g) were added to a suspension of Intermediate 59 (0.9 g; 1.2 mmoles), prepared as described in example 29, in ethanol 95% (240 ml).

The mixture was kept under stirring under hydrogen pressure (2.7 atm) at room temperature for 16 hours, then water (250 ml) was added and the catalyst was filtered off and washed on the filter with water.

The solvents were removed under reduced pressure obtaining Compound 39 (0.6 g) as a white amorphous solid.

$^1$H-NMR (200 MHz; $D_2O$): δ(ppm): 0.78 (t, 3H); 1.14–2.16 (m, 12H); 2.34–3.17 (m, 14H); 3.39–3.54 (m, 1H); 6.46 (d, 1H); 6.59 (d, 1H); 7.20–7.58 (m, 4H).

Mass (thermospray): 505 [M+1].

EXAMPLE 47

Preparation of (S)-N-propyl-N-[6-[2-(2-amino-1,3-benzothiazol-6-yl)ethylamino]hexyl]-5,6-dihydroxy-1,2,3,4-tetrahydro-2-naphthylamine trihydrochloride (Compound 40)

A boron trichloride 1M solution in $CH_2Cl_2$ (27 ml) was added dropwise at −35° C. to a stirred solution of Intermediate 52 (0.9 g; 1.4 mmoles), prepared as described in example 24, in chloroform (44 ml) under nitrogen.

The reaction mixture was kept under stirring at −30° C. for 15 minutes, then heated at 50° C. and kept under stirring for 4 hours. Methanol (30 ml) was added and the solvents were removed under reduced pressure.

The residue was purified by chromatography (eluent $CH_2Cl_2$:$CH_3OH$:HCOOH 50%=80:20:1).

The resultant solid was dissolved in absolute ethanol and the solution was acidified to pH 1 by adding a solution of HCl in ethyl ether (15% w/v).

Evaporation of the solvents under reduced pressure gave Compound 40 (0.54 g) as a white amorphous solid.

$^1$H-NMR (200 MHz; $D_2O$): δ(ppm): 0.80 (t, 3H); 1.19–2.17 (m, 12H); 2.36–3.19 (m, 14H); 3.42–3.57 (m, 1H); 6.47 (d, 1H); 6.60 (d, 1H); 7.20–7.48 (m, 3H).

Mass: 497 [M+1].

EXAMPLE 48

Evaluation of the affinity towards $D_1$ and $D_2$ receptors Receptor binding

Brains of Sprague-Dawley male rats (200–250 g) were removed and the membranes of striated tissues were prepared according to the method described by Billard et al. in Life Sciences, 35, 1885, (1984).

The tissue were homogenized in 50 mM Tris/HCl buffer at pH 7.4 (1:100 w/v).

The homogenate was centrifuged and the pellet resuspended, recentrifuged and resuspended again in 50 mM Tris/HCl buffer at pH 7.4 containing 120 mM NaCl, 5 mM KCl, 2 mM $CaCl_2$ and 1 mM $MgCl_2$.

The affinity towards $D_1$ receptor and $D_2$ receptor was evaluated by using [$^3$H]-SCH23390 [R(+)-8-chloro-2,3,4,5-tetrahydro-3-methyl-5-phenyl-1H-3-benzazepine 7-ol hydrochloride] and [$^3$H]-domperidone (The Merck Index—XI ed., no. 3412, page 537) respectively as labelled ligands.

Dopamine, dopexamine and (S)-N-propyl-N-[6-[2-(2-methoxyphenyl)ethylamino]hexyl]-5,6-dihydroxy-1,2,3,4-tetrahydro-2-naphthylamine dihydrochloride (Ref. A), described in example 6 of the International patent application WO 93/19036, were used as reference substances.

The conditions of standard incubation (volume 1000 μl) for the test in which [$^3$H]-SCH23390 was used were the following: 50 mM Tris/HCl buffer (pH 7.4), 0.2 nM [$^3$H]-SCH23390, a membrane preparation of 130–140 μg proteins/ml.

The mixture was incubated with different concentrations of the tested compounds at 37° C. for 20 minutes, filtered under vacuum through Whatman GF/C filters and then washed 4 times with 5 ml of 50 mM Tris/HCl buffer (pH 7.4) cooled with ice.

For the affinity studies towards $D_2$ receptor, [$^3$H]-domperidone (0.3 nM) was incubated in a volume of 1000 μl containing buffer and membrane preparation as above described.

Furthermore, bovine serum albumine (BSA) (0.01%) was added.

The mixture was incubated at 37° C. for 30 minutes for each concentration of tested compounds.

The obtained results, expressed as $K_1$ (nM), for compounds 1–10, 13, 15–16, 24–25 and 34, Ref. A, dopamine and dopexamine were reported in the following table.

TABLE 1

Affinity [$K_1$ (nM)] of compounds 1–10, 13, 15–16, 24–25 and 34, Ref. A, dopamine and dopexamine towards $D_1$ and $D_2$ receptors determined by binding studies on rat striated membranes.

|  | $D_1$ [$^3$H]-SCH23390 | $D_2$ [$^3$H]-domperidone |
|---|---|---|
| Compound 1 | 49 | 0.66 |
| Compound 2 | 25 | 0.4 |
| Compound 3 | 69 | 0.31 |
| Compound 4 | 78 | 1.1 |
| Compound 5 | 69 | 1.5 |
| Compound 6 | 81 | 1.3 |
| Compound 7 | 370 | 0.25 |
| Compound 8 | 23 | 0.1 |
| Compound 9 | 22 | 0.15 |
| Compound 10 | 117 | 0.6 |
| Compound 13 | 29 | 0.4 |
| Compound 15 | 119 | 0.24 |
| Compound 16 | 178 | 0.2 |
| Compound 24 | 45 | 1.8 |
| Compound 25 | 130 | 0.6 |
| Compound 34 | 356 | 2.1 |
| Ref. A | 158 | 0.8 |
| Dopamine | 3200 | 1500 |
| Dopexamine | 3200 | 1220 |

The compounds object of the present invention show a high affinity towards both receptor subtypes resulting much more affine than dopamine and dopexamine and with an affinity at least comparable with that of Ref. A on both $D_1$ and $D_2$ receptors.

EXAMPLE 49

Dopaminergic functional studies on isolated tissues Evaluation of $D_1$-like activity in the Rabbit Splenic Artery (RSA) test Arterial rings were prepared according to Semeraro et al., Naunyn. Schmied. Arch. Pharmacol., 1990, 342, 539.

The arterial preparations were contracted with U46619 (9,11-di-deoxy-11α,9α-epoxy-methanoprostaglandin $F_{2α}$) at the submaximal concentration 0.1 µM.

The tested compounds were cumulatively administered.

Ref. A was used as reference substance.

Agonist activity evaluated at the peak of the effect and expressed as potency ratio ($EC_{50}$ of Ref. A/$EC_{50}$ of tested compound) is reported in table 2.

Evaluation of $D_2$-like activity in the Rabbit Ear Artery (REA) test

Arterial rings were prepared according to the method described by Steinsland et al., Science, 1978, 443, 199, modified as follows. Male New Zealand rabbits weighing 2.5–3 Kg were sacrificed by intravenous injection of an excess of pentobarbital sodium and exsanguinated. The two ears were taken away and the central ear artery was dissected into 3 mm long rings.

These preparations were set up in a 25 ml organ bath containing Krebs solution (mM/l): NaCl 118, KCl 4.7, $CaCl_2$ 2.5, $MgSO_4$ 1.2, $NaHCO_3$ 25, $KH_2PO_4$ 1.2, glucose 11.1, equilibrated with 95% $O_2$–5% $CO_2$ and maintained at 35°±1° C.

Krebs solution was medicated with EDTA (10 µM) to prevent cathecolamine oxydation, desipramine (0.1 µM) and corticosterone (30 µM), to block neuronal and extraneuronal cathecolamine uptake. The preparations were electrically stimulated (10 Hz, 1 msec, 40–80 mA, 500 msec duration) at 5 minutes intervals.

The tested compounds were cumulatively administered.

Ref. A was used as reference substance.

Agonist activity evaluated at the peak of the effect and expressed as potency ratio ($EC_{50}$ of Ref. A/$EC_{50}$ of tested compound) is reported in table 2.

TABLE 2

$D_1$-like and $D_2$-like activity of compounds 2, 6, 8–19, 21–22, 24–27, 29, 31–37, 39–40 and Ref. A determined by RSA and REA tests respectively, expressed as potency ratio ($EC_{50}$ of Ref. A/$EC_{50}$ of tested compound).

|  | $D_1$-like (RSA) potency ratio | $D_2$-like (REA) potency ratio |
|---|---|---|
| Compound 2 | 10 | 0.3 |
| Compound 6 | 10 | 3 |
| Compound 8 | 1 | 1.7 |
| Compound 9 | 10 | 5 |
| Compound 10 | 1.4 | 2 |
| Compound 11 | 25 | 4 |
| Compound 12 | 5 | — |
| Compound 13 | 10 | 14 |
| Compound 14 | 33 | 3 |
| Compound 15 | 0.9 | 0.5 |
| Compound 16 | 3 | 0.8 |
| Compound 17 | 12 | 25 |
| Compound 18 | 50 | 5 |
| Compound 19 | 11 | 4 |
| Compound 21 | 3 | 1.7 |
| Compound 22 | 14 | 3 |
| Compound 24 | 17 | 3 |
| Compound 25 | 1.7 | 1.3 |
| Compound 26 | 33 | 10 |
| Compound 27 | 25 | 4 |
| Compound 29 | 50 | 1.7 |
| Compound 31 | 100 | 5 |
| Compound 32 | 33 | 10 |
| Compound 33 | 5 | 5 |
| Compound 34 | 2.5 | 5 |
| Compound 35 | 2 | 0.4 |
| Compound 36 | 4.5 | 12 |
| Compound 37 | 5 | 5 |
| Compound 39 | 2.5 | 3 |
| Compound 40 | 14 | 3 |
| Ref. A | 1 | 1 |

The above data show that the compounds of formula I, object of the present invention, have a very significant dopaminergic activity, up to 100 times higher than that of Ref. A.

EXAMPLE 50

In vivo hypertensive activity

Male spontaneously hypertensive rats (Charles River) more than 14 weeks old were used.

Catheters were inserted into the right carotid artery and into the left giugular vein under barbituric anesthesia.

The animals were allowed to recover overnight.

The tested compounds were administered into the left giugular vein by bolus injection.

Control animals were injected with an equal volume of vehicle. The induced effect was continuously recorded over a period of 4 hours.

Basal values of Mean Blood Pressure (MBP) were in the range of 190–200 mmHg.

The antihypertensive activity of compound 22 expressed as MBP reduction compared with the antihypertensive activity of Ref. A is reported in the following table.

TABLE 3

| In vivohypertensive activity of Compound 22 and Ref. A after i.v. administration. | | |
|---|---|---|
| | Ref. A (30 nmol/kg) (n = 6) | Compound 22 (30 nmol/kg) (n = 7) |
| MBP reduction (mmHg) mean ± S.E. | −25 ± 1.1 | −61.7 ± 5.7 |

We claim:

1. A compound of formula

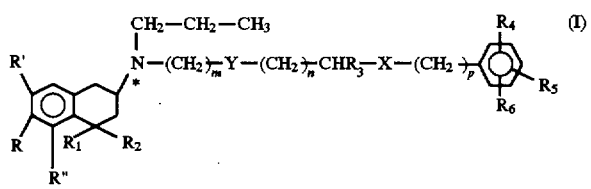

wherein m is an integer number selected from 4, 5, 6, 7 and 8;

R, R' and R" are hydrogen atoms or OH groups, provided that at least one among R, R' and R" is a hydrogen atom but R, R' and R" are not all contemporaneously hydrogen atoms and R' and R" are not both contemporaneously OH groups; or one of R' and R" is a NHCHO, $NHCH_3$, $NHSO_2CH_3$, $CH_2OH$ or $CH_3$ group and the other is hydrogen;

$R_1$ and $R_2$, the same or different, are hydrogen atoms, $C_1$–$C_3$ alkyl groups or, together with the carbon atom to which they are bonded, form a cyclopropyl;

n is an integer number selected from 0, 1, 2, 3 and 4;

p is an integer number selected between 0 and 1;

$R_3$ is a hydrogen atom or a $C_1$–$C_4$ alkyl group;

Y is S, O, $N(R_7)CO$, $CO(R_7)N$ or $N(R_7)$;

X is $N(R_8)$, O, S, SO, $SO_2$, CO or a single bond;

$R_4$, $R_5$ and $R_6$, the same or different, are hydrogen, OH, halogen, $C_1$–$C_4$ alkyl, $C_1$–$C_4$ alkoxy, nitro, $C_1$–$C_4$ alkylthio, $NH_2$, mono- or di-$C_1$–$C_4$ alkylamino, SH, $C_1$–$C_4$ alkylsulphonyl, $C_1$–$C_4$ alkoxycarbonyl, NHCHO, $C_1$–$C_4$ alkylcarbonylamino, $NHCONH_2$, $C_1$–$C_4$ alkylsulphonylamino, $C_1$–$C_4$ alkylaminosulphonyl, $SO_2NH_2$, $NHSO_2NH_2$, COOH, $SO_3H$, $CONH_2$, $CH_2OH$ or phenyl; or $R_4$ and $R_5$, in ortho position one with respect to the other, together form an optionally unsaturated chain made by 3 or 4 groups selected among $CR'''R^{IV}$, CO, S, O and $NR^V$, wherein R''' is a hydrogen atom or a $C_1$–$C_4$ alkyl group, $R^{IV}$ is a hydrogen atom, a $C_1$–$C_4$ alkyl group or an amino group and $R^V$ is a hydrogen atom or a $C_1$–$C_4$ alkyl group; or R''' together with a vicinal R''' or $R^V$ constitutes a single bond or $R^V$ together with a vicinal R''' or $R^V$ constitutes a single bond;

$R_7$ is a hydrogen atom or a $C_1$–$C_4$ alkyl group;

$R_8$ is a hydrogen atom; and $R_4$, when in ortho position with respect to X, can form a —$CH_2$—O— chain with $R_3$;

the asterisk marks an asymmetric carbon atom;

provided that when p=1, X is an $N(R_8)$ group; and provided that when R and R' or R" are OH groups, $R_1$ and $R_2$ are hydrogen atoms and a) when Y is $N(R_7)$, $R_7$ is hydrogen or alkyl and $R_3$ is hydrogen, at least one among $R_4$, $R_5$ and $R_6$ is different from hydrogen, halogen, $C_1$–$C_4$ alkyl and $C_1$–$C_4$ alkoxy;

b) when Y is $N(R_7)$, $R_7$ is hydrogen or alkyl, $R_3$ is hydrogen and X is a simple bond, at least one among $R_4$, $R_5$ and $R_6$ is different from hydrogen, halogen, $NH_2$, $C_1$–$C_4$ alkyl, $C_1$–$C_4$ alkoxy and nitro;

c) when Y is $N(R_7)$, $R_7$ is hydrogen or alkyl, n is 1, $R_3$ is hydrogen and X is a simple bond, at least one among $R_4$, $R_5$ and $R_6$ is different from hydrogen and from OH;

and pharmaceutically acceptable salts thereof.

2. A compound according to claim 1 wherein R' is a hydrogen atom, R and R" are OH groups and the carbon atom marked by an asterisk has configuration.

3. A compound according to claim 1 wherein R', $R_1$ and $R_2$ are hydrogen atoms, R and R" are OH groups, m is 6 and the carbon atom marked by an asterisk has S configuration.

4. A compound according to claim 1 wherein $R_4$, $R_5$ and $R_6$, the same or different, are hydrogen, OH, methoxy, methyl, nitro, chloro, methylsulphonyl, $NH_2$, $SO_2NH_2$, methylsulphonylamino, $NH_2CONH_2$, methoxcarbonyl, acetylamino, $CONH_2$, $CH_2OH$, and $SO_3H$ or $R^4$ and $R_5$, in ortho position one with respect to the other, form a chain of formula —S—CO—$NR'^V$— wherein $R'^V$ is a hydrogen atom, or methylendioxy.

5. A compound according to claim 1 in optically active form.

6. A pharmaceutical composition containing a therapeutically effective amount of a compound according to claim 1 in admixture with a suitable carrier.

7. A method for the treatment of a cardiovascular disease comprising administering to a patient in need thereof a therapeutically effective amount of a compound of claim 1.

8. A method for the treatment of arterial hypertension, congestive heart failure, renal failure, peripheral arteriopathies or cerebrovascular insufficiencies to a patient in need thereof a therapeutically effective amount of a compound according to claim 1.

* * * * *